United States Patent
Iwakuma et al.

(10) Patent No.: US 7,235,312 B2
(45) Date of Patent: Jun. 26, 2007

(54) AROMATIC COMPOUNDS AND ORGANIC ELECTROLUMINESCENT DEVICES MADE BY USING THE SAME

(75) Inventors: Toshihiro Iwakuma, Chiba (JP); Takashi Arakane, Chiba (JP); Tadashi Kusumoto, Chiba (JP)

(73) Assignees: Petroleum Energy Center, A Juridical Incorporated Foundation, Tokyo (JP); Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/483,990

(22) PCT Filed: Jul. 12, 2002

(86) PCT No.: PCT/JP02/07103

§ 371 (c)(1), (2), (4) Date: Jan. 23, 2004

(87) PCT Pub. No.: WO03/010127

PCT Pub. Date: Jun. 2, 2003

(65) Prior Publication Data

US 2004/0191563 A1    Sep. 30, 2004

(30) Foreign Application Priority Data

Jul. 23, 2001    (JP) .............................. 2001-220946

(51) Int. Cl.
*H01J 1/62* (2006.01)
*C07C 211/00* (2006.01)

(52) U.S. Cl. ..................... 428/690; 428/917; 313/504; 313/506; 564/426

(58) Field of Classification Search ................ 428/690, 428/917; 257/E51.051, 40, E51.03; 313/504, 313/506; 564/426; 546/7; 514/727; 558/343
See application file for complete search history.

(56) References Cited

U.S. PATENT DOCUMENTS 6,803,120 B2 * 10/2004 Fukuoka et al. ............ 428/690
6,815,090 B1 * 11/2004 Tagami et al. .............. 428/690
6,866,947 B1 * 3/2005 Fukuoka et al. ............ 428/690

FOREIGN PATENT DOCUMENTS

| WO | 01/23497 | 4/2001 |
|---|---|---|
| WO | 01/48116 | 7/2001 |
| WO | 01/76323 | 10/2001 |
| WO | 02/20693 | 3/2002 |
| WO | 02/52904 | 7/2002 |

* cited by examiner

*Primary Examiner*—Rena Dye
*Assistant Examiner*—C Thompson
(74) *Attorney, Agent, or Firm*—Oblon, Spivak, McClelland, Maier & Neustadt, P.C.

(57) ABSTRACT

A novel aromatic compound represented by following general formula (I):

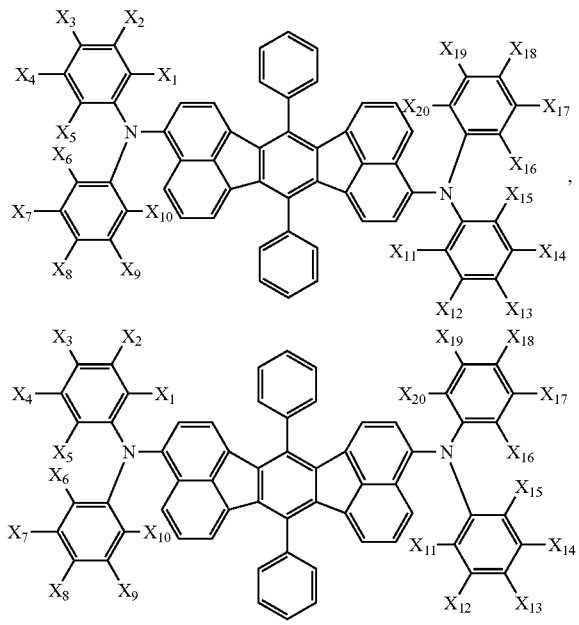

among $X_1$ to $X_{20}$ in general formula (I), (1) at least four each independently represent a linear or branched alkoxyl group having 1 to 6 carbon atoms, and others each represent hydrogen atom; (2) at least one represents a linear or branched alkyl group having 1 to 6 carbon atoms, at least one represents a linear or branched alkoxyl group having 1 to 6 carbon atoms, a total of a number of the alkyl group and a number of the alkoxyl group being 4 or greater, and others each represent hydrogen atom; (3) at least six each independently represent a linear or branched alkyl group having 1 to 6 carbon atoms, and others each represent hydrogen atom; or (4) at least four each independently represent a linear or branched alkyl group having 1 to 6 carbon atoms, two among said alkyl groups having 3 to 6 carbon atoms, and others each represent hydrogen atom; and an organic electroluminescence device using the aromatic compound, are provided. The device exhibits excellent purity of color, provides great luminance of emitted light and efficiency of light emission even at a small driving voltage, has a long lifetime and emits reddish light.

4 Claims, No Drawings

AROMATIC COMPOUNDS AND ORGANIC ELECTROLUMINESCENT DEVICES MADE BY USING THE SAME

TECHNICAL FIELD

The present invention relates to a novel aromatic compound and an organic electroluminescence device using the compound and, more particularly, to an organic electroluminescence device which exhibits excellent purity of color, provides great luminance of emitted light and efficiency of light emission, has a long lifetime and emits reddish light and a novel aromatic compound utilized for the electroluminescence device.

Background Art

Organic electroluminescence ("electroluminescence" will be referred to as "EL", hereinafter) devices which utilize organic substances are expected to be useful for application as an inexpensive full color display device of the solid light emission type having a great size, and various developments on the organic EL devices are being conducted. In general, an organic EL device has a construction comprising a light emitting layer and a pair of electrodes disposed at both sides of the light emitting layer. When an electric field is applied between the two electrodes, electrons are injected from the cathode side and holes are injected from the anode side. The electrons are recombined with the holes in the light emitting layer to form an excited state, and the energy generated when the excited state returns to the ground state is emitted as light.

At present, the device for a full-color display is still under development even though the actual use of organic EL devices has started. In particular, a light emitting material for organic EL devices which exhibits excellent purity of color of emitted light, provides a great efficiency of light emission, has a long lifetime and emits reddish light has been desired.

As the attempt to satisfy the above desire, a device emitting red light in which a derivative of naphthacene or pentacene is added to a light emitting layer is disclosed in Japanese Patent Application Laid-Open No. Heisei 8(1996)-311442. Although this device exhibits an excellent purity of red light, the device requires an applied voltage as great as 11 V and has an insufficient half luminance lifetime of about 150 hours. A device in which a compound derived from dicyanomethylene (DCM) is added to a light emitting layer is disclosed in Japanese Patent Application Laid-Open No. Heisei 3(1991)-162481. However, this device exhibits an insufficient purity of red light. In Japanese Patent Application Laid-Open No. 2001-81451, a device emitting red light in which an amine-based aromatic compound is added to a light emitting layer is disclosed. However, this light emitting device requires a high applied voltage although the device exhibits excellent purity of color such as a CIE chromaticity of (0.64, 0.33). In WO 01/23497, a device in which a compound represented by general formula (I) shown below, in which four of $X_1$ to $X_{20}$ each represent methyl group, is added to the light emitting layer is disclosed. However, the color of the emitted light is reddish orange, and the chromaticity is insufficient.

DISCLOSURE OF THE INVENTION

The present invention has been made to overcome the above problems and has an object of providing an organic EL device which exhibits excellent purity of color, provides great luminance of emitted light and efficiency of light emission even at a small driving voltage, has a long lifetime and emits reddish light and a novel aromatic compound utilized for the organic EL device.

As the result of intensive studies by the present inventors to achieve the above object, it was found that a device which could exhibit excellent purity of color, provides great luminance of emitted light and efficiency of light emission even at a small driving voltage and has a long lifetime could be provided by further introducing an electron-donating substituent into diphenylamino group bonded to the mother skeleton structure having a specific structure. The present invention has been completed based on this knowledge.

The present invention provides a novel aromatic compound represented by following general formula (I):

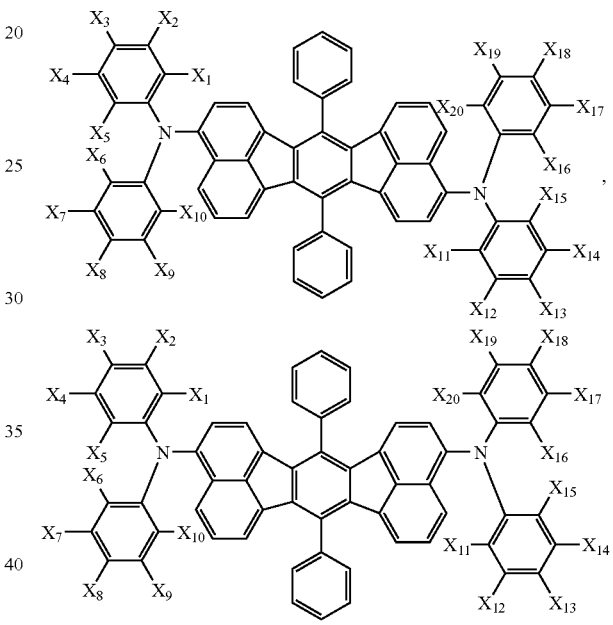

wherein general formula (I) satisfies any one of following conditions (1) to (4):

(1) Among $X_1$ to $X_{20}$, at least four each independently represent a linear or branched alkoxyl group having 1 to 6 carbon atoms, and others each represent hydrogen atom;

(2) Among $X_1$ to $X_{20}$, at least one represents a linear or branched alkyl group having 1 to 6 carbon atoms, at least one represents a linear or branched alkoxyl group having 1 to 6 carbon atoms, a total of a number of the alkyl group and a number of the alkoxyl group being 4 or greater, and others each represent hydrogen atom;

(3) Among $X_1$ to $X_{20}$, at least six each independently represent a linear or branched alkyl group having 1 to 6 carbon atoms, and others each represent hydrogen atom; and (4) Among $X_1$ to $X_{20}$, at least four each independently represent a linear or branched alkyl group having 1 to 6 carbon atoms, two alkyl groups among said alkyl groups having 3 to 6 carbon atoms, and others each represent hydrogen atom.

The present invention also provides an organic electroluminescence device which comprises a pair of electrodes and an organic compound layer which comprises a light emitting layer or a plurality of layers comprising a light emitting layer and is disposed between the pair of electrodes, wherein at least one layer in the organic compound layer comprises an aromatic compound represented by general formula (I) described above.

THE MOST PREFERRED EMBODIMENT TO CARRY OUT THE INVENTION

The novel aromatic compound of the present invention satisfies one of the following conditions (1) to (4) in general formula (I) described above:

(1) Among $X_1$ to $X_{20}$, at least four each independently represent a linear or branched alkoxyl group having 1 to 6 carbon atoms, and others each represent hydrogen atom.

(2) Among $X_1$ to $X_{20}$, at least one represents a linear or branched alkyl group having 1 to 6 carbon atoms, at least one represents a linear or branched alkoxyl group having 1 to 6 carbon atoms, a total of a number of the alkyl group and a number of the alkoxyl group being 4 or greater, and others each represent hydrogen atom.

(3) Among $X_1$ to $X_{20}$, at least six each independently represent a linear or branched alkyl group having 1 to 6 carbon atoms, and others each represent hydrogen atom.

(4) Among $X_1$ to $X_{20}$, at least four each independently represent a linear or branched alkyl group having 1 to 6 carbon atoms, two alkyl groups among said alkyl groups having 3 to 6 carbon atoms, and others each represent hydrogen atom.

In general formula (I) described above, examples of the alkyl group having 1 to 6 carbon atoms include methyl group, ethyl group, n-propyl group, isopropyl group, n-butyl group, t-butyl group, s-butyl group, isobutyl group, n-pentyl group, 1-methylbutyl group, 2-methylbutyl group, 3-methylbutyl group, 1-ethylpropyl group, 2-pentyl group, 3-pentyl group, 2,2-dimethylpropyl group and n-hexyl group. Among these groups, methyl group, ethyl group, n-propyl group, isopropyl group, n-butyl group, t-butyl group, s-butyl group and isobutyl group are preferable.

Examples of the alkoxyl group having 1 to 6 carbon atoms include methoxy group, ethoxy group, n-propoxy group, isopropoxy group, n-butoxy group, t-butoxy group, s-butoxy group, isobutoxy group, n-pentoxy group, 2-pentoxyl group, 3-pentoxy group 2,2-dimethylpropoxy group and n-hexoxy group. Among these groups, methoxy group, ethoxy group, n-propoxy group, isopropoxy group, n-butoxy group, t-butoxy group, s-butoxy group and isobutoxy group are preferable.

Specific examples of the aromatic compounds represented by general formula (I) of the present invention are shown in the following. However, the aromatic compound of the present invention is not limited to the compounds shown as the examples. In the following formulae, Me represents methyl group, Et represents ethyl group, Pr represents propyl group, Bu represents butyl group, and Hex represents hexyl group.

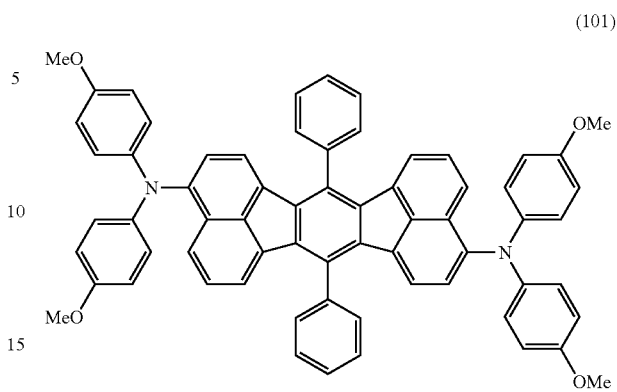

(101)

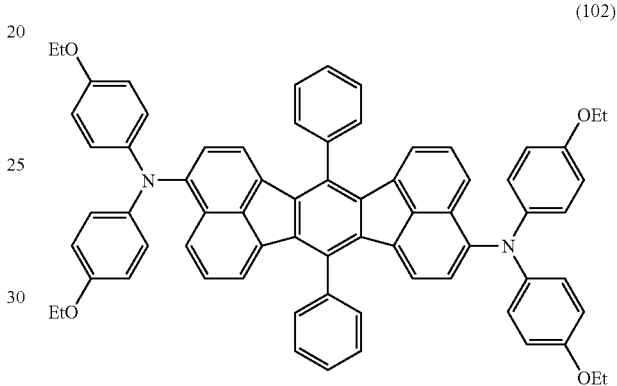

(102)

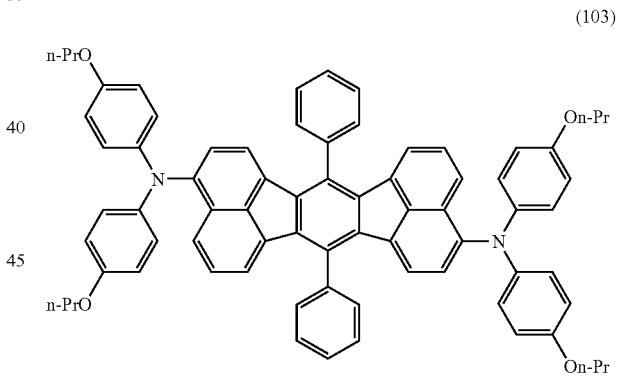

(103)

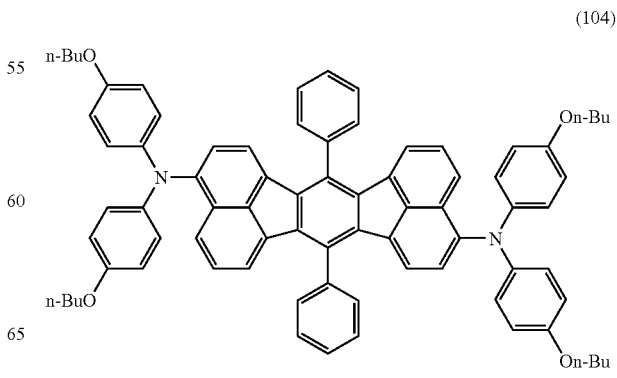

(104)

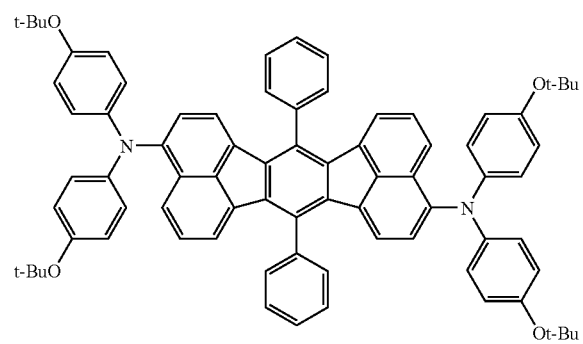
(105)
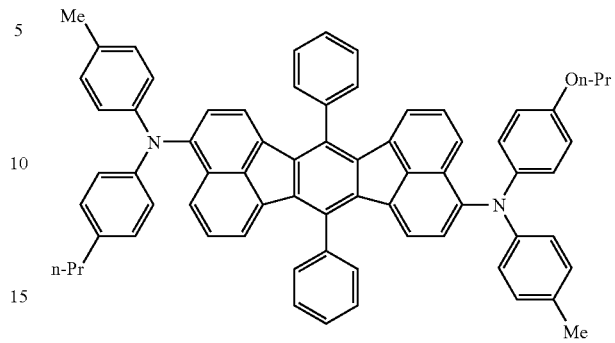
(109)
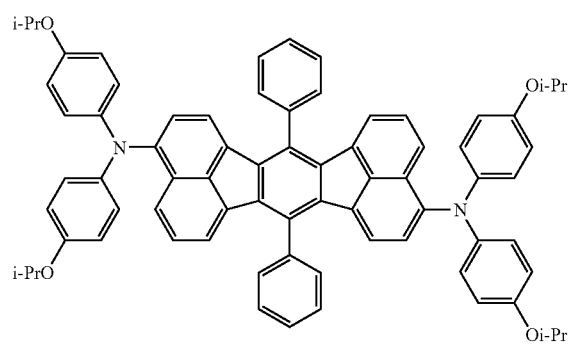
(106)
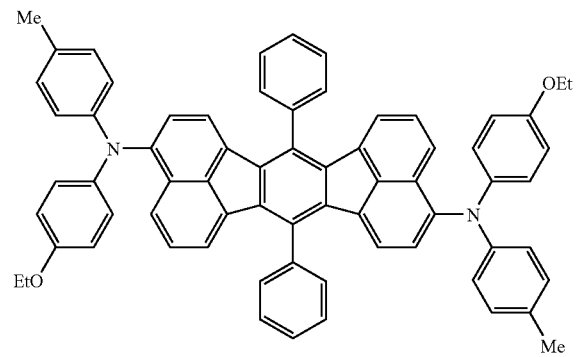
(110)
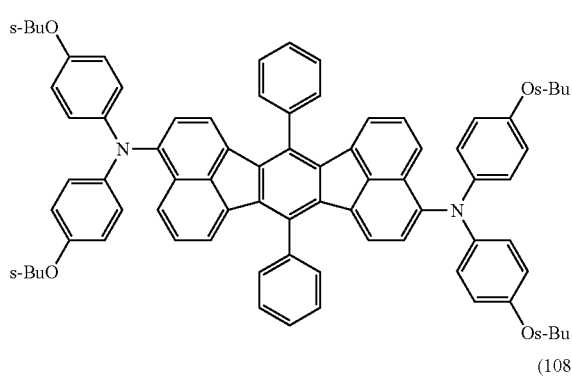
(107)
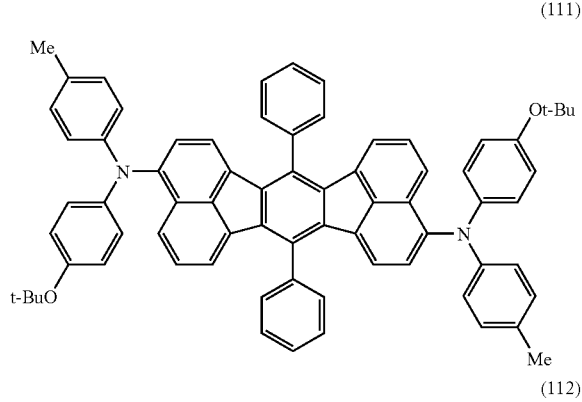
(111)
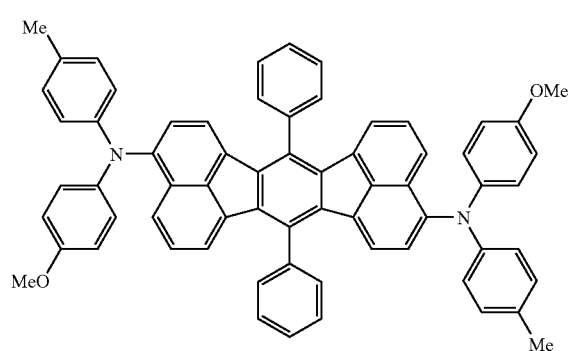
(108)
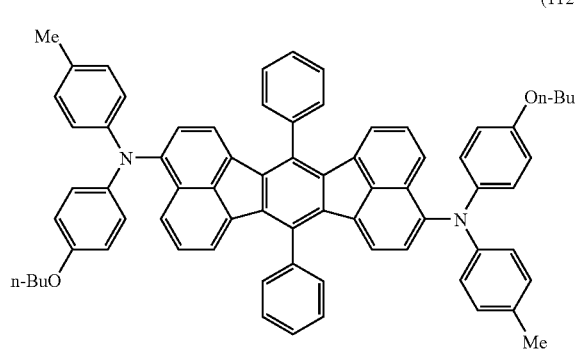
(112)

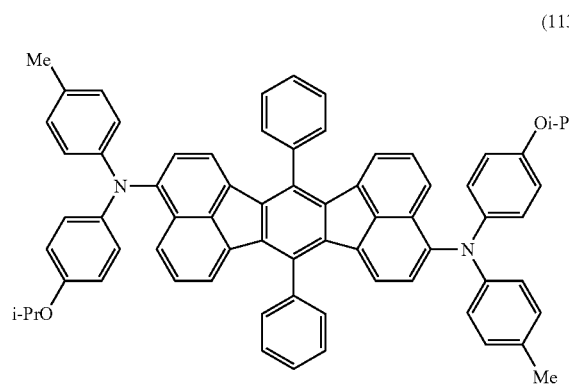
(113)
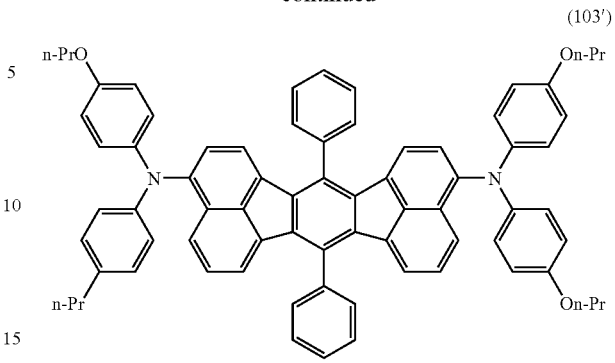
(103')
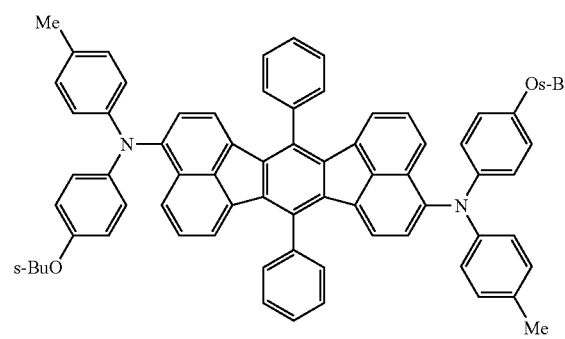
(114)
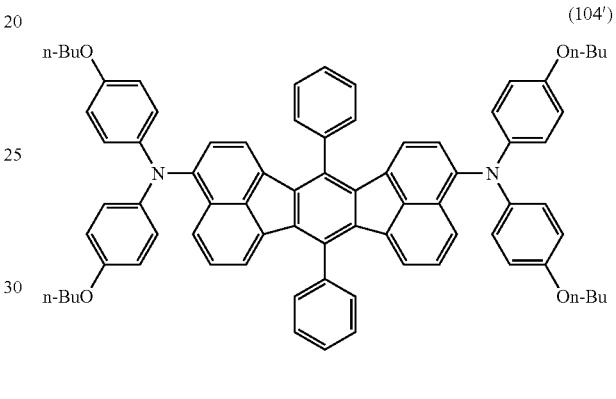
(104')
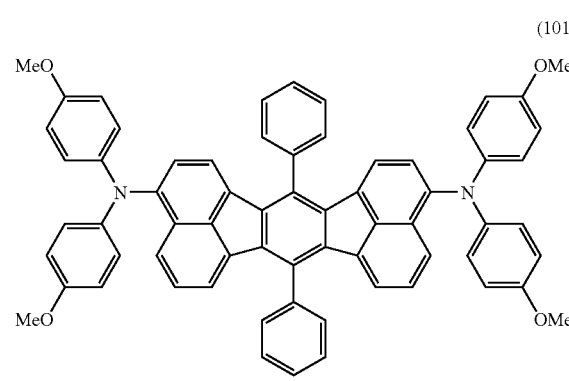
(101')
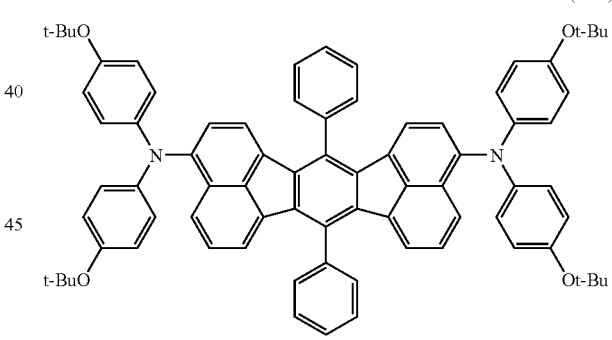
(105')
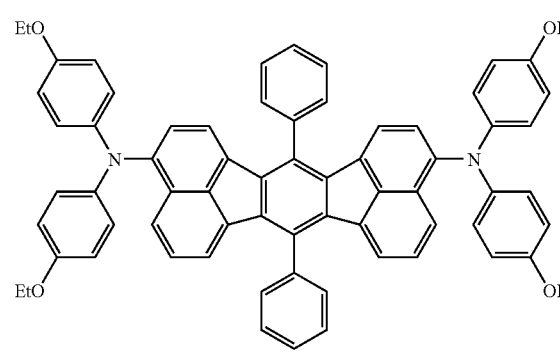
(102')
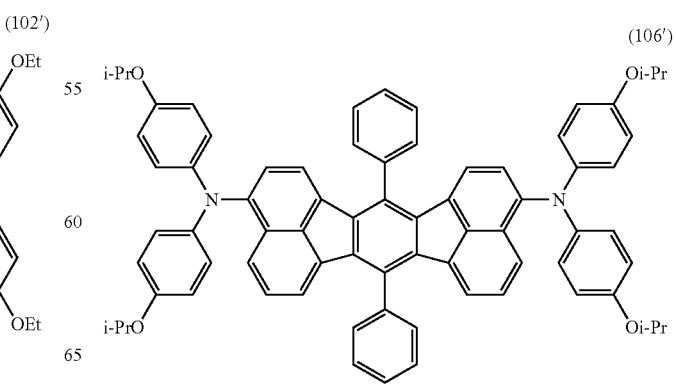
(106')

-continued
(107′)
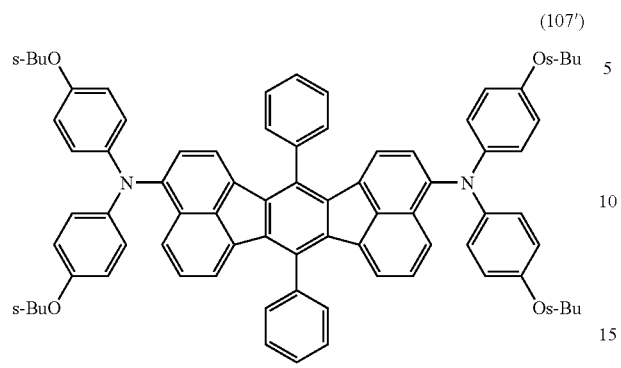
(108′)
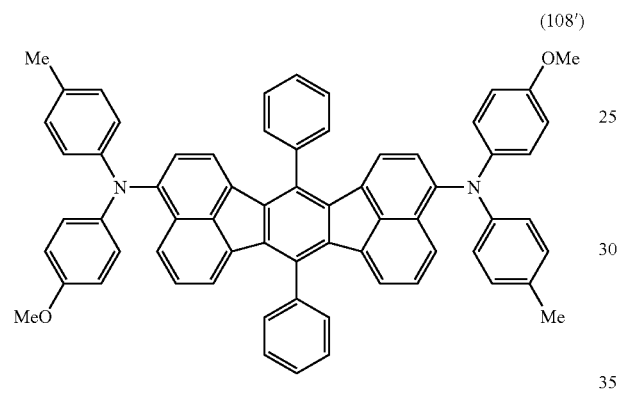
(109′)
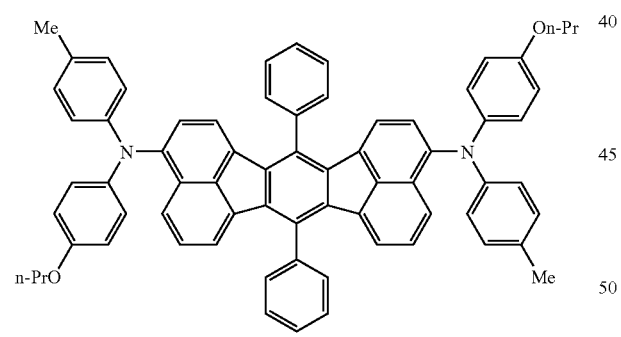
(110′)
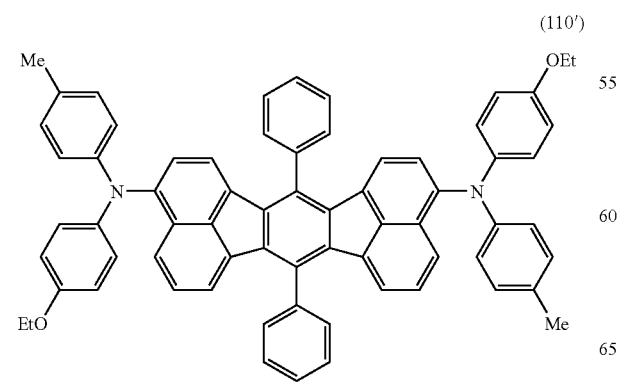
-continued
(111′)
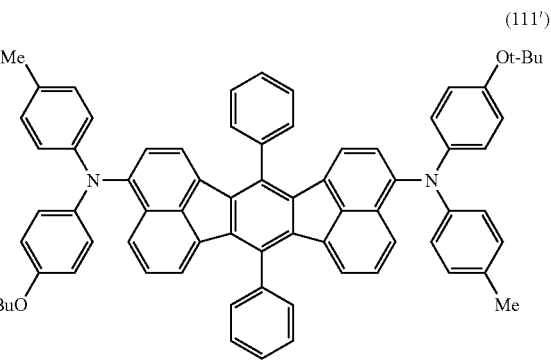
(112′)
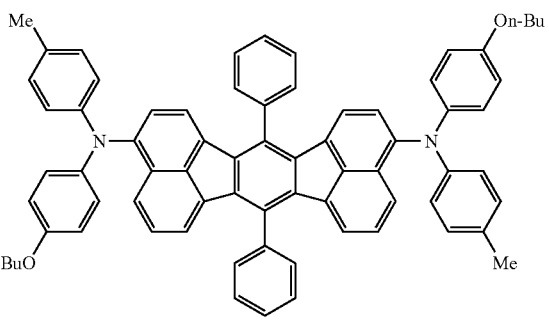
(113′)
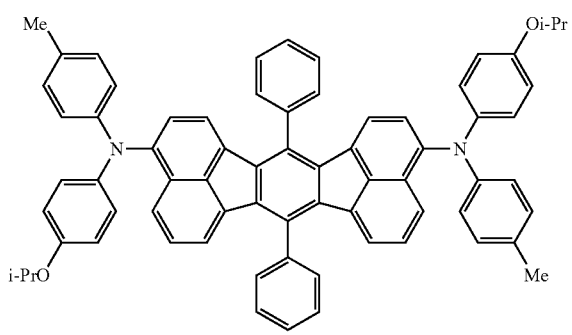
(114′)
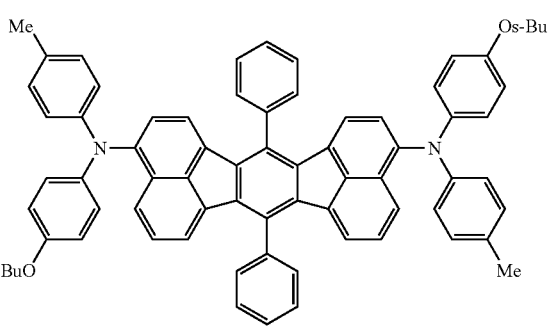

-continued
(201)
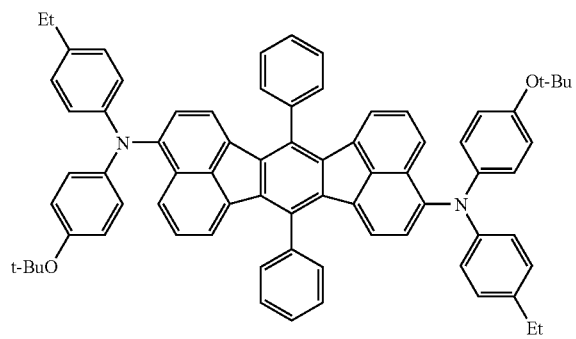
(202)
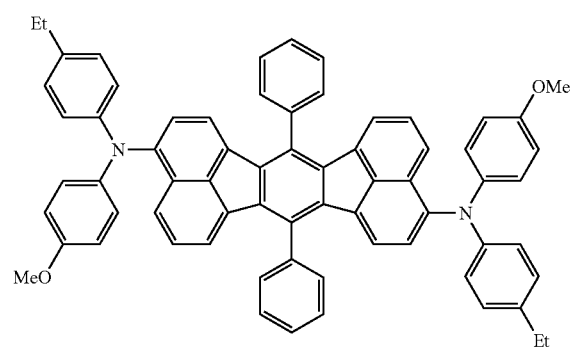
(203)
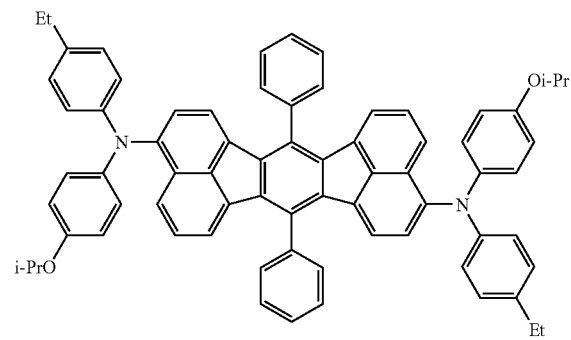
(204)
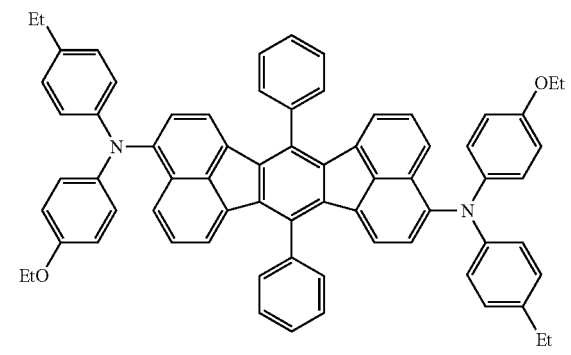
-continued
(205)
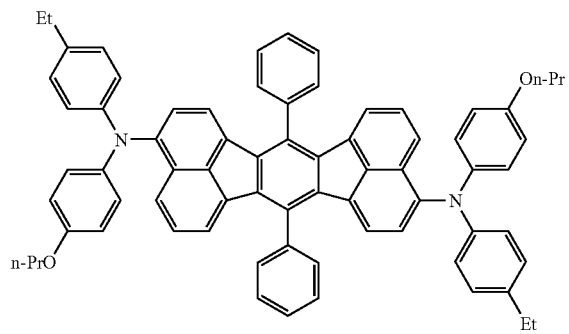
(206)
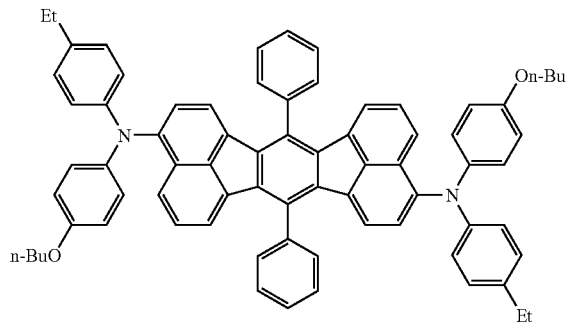
(207)
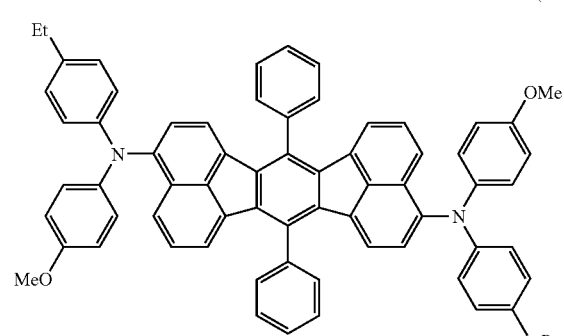
(208)
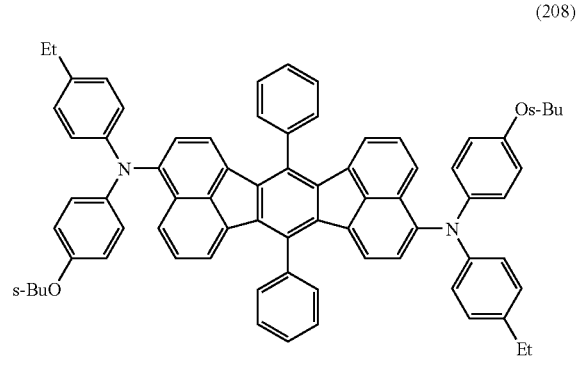

-continued
(209)
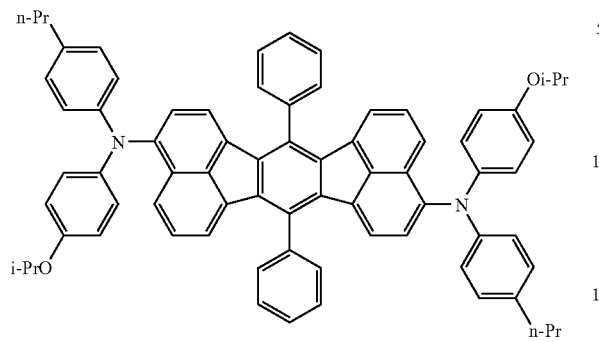
(210)
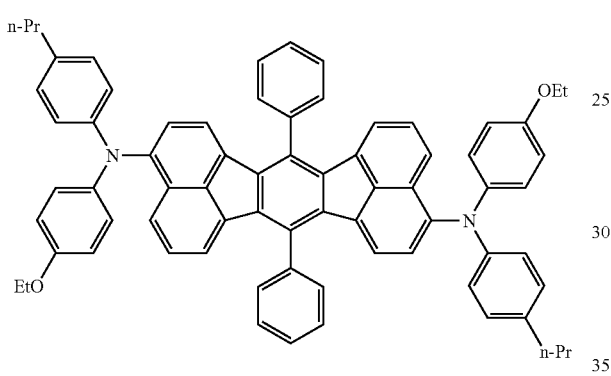
(211)
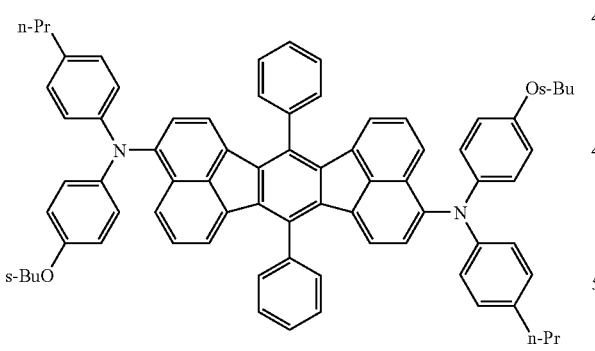
(212)
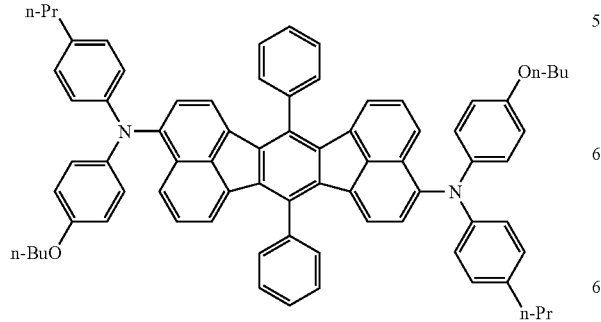
-continued
(213)
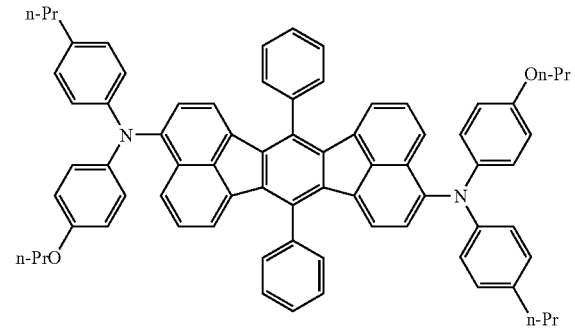
(214)
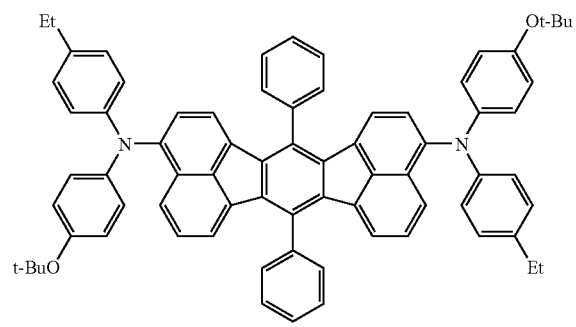
(201')
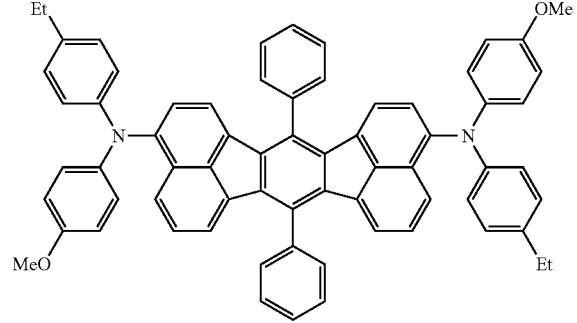
(202')

-continued
(203′)
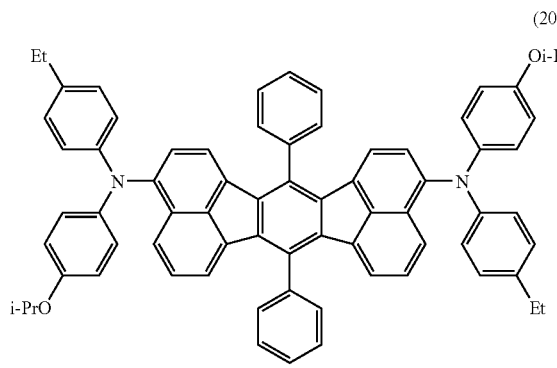
(207′)
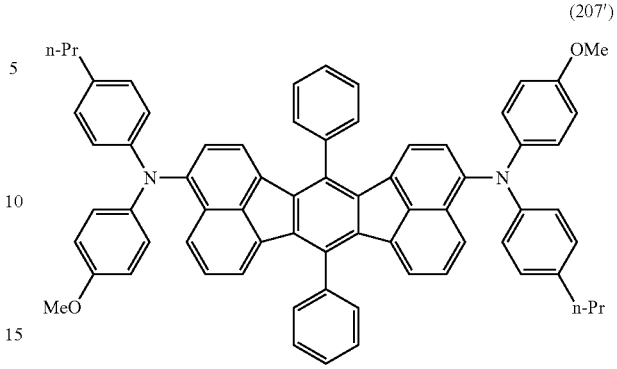
(204′)
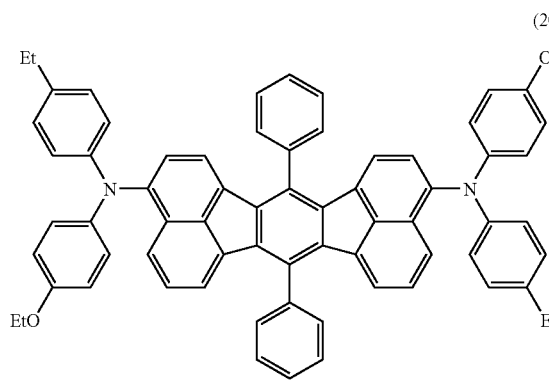
(208′)
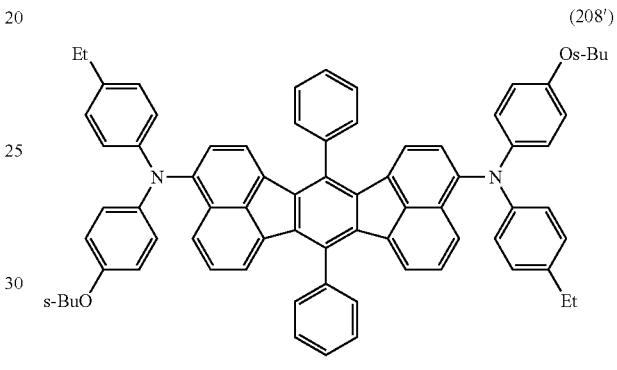
(205′)
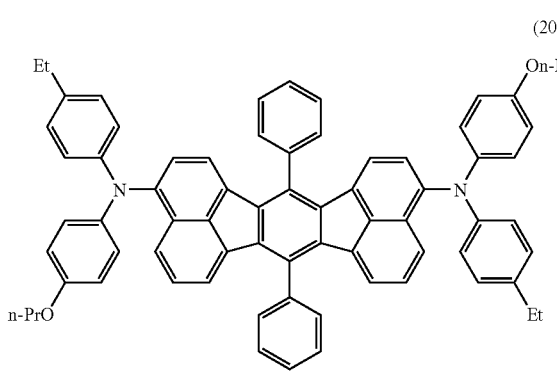
(209′)
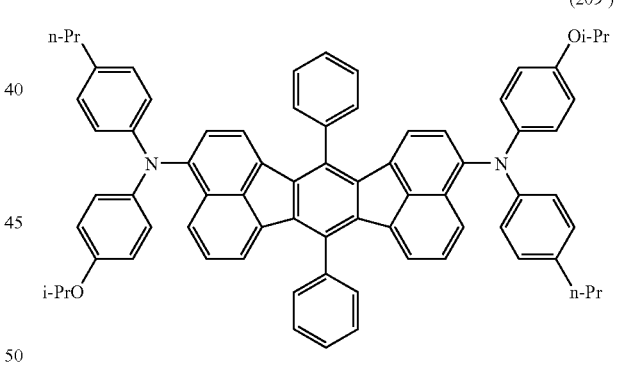
(206′)
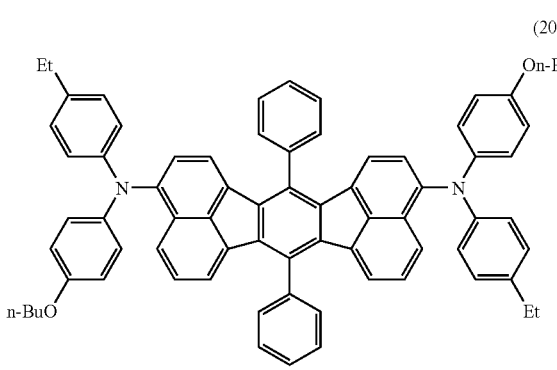
(210′)
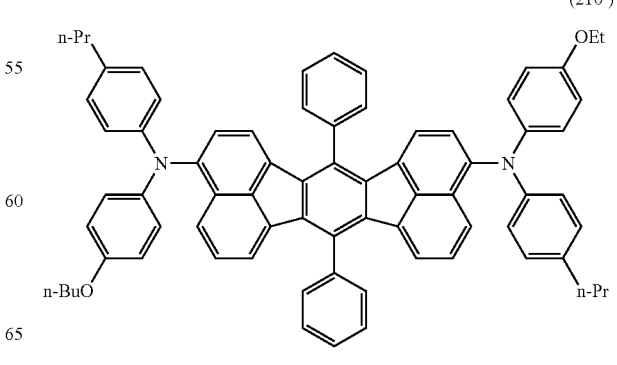

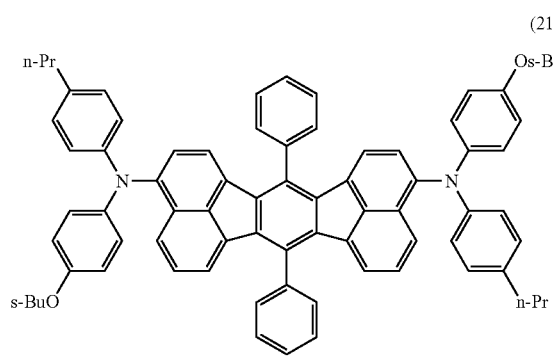
(211′)
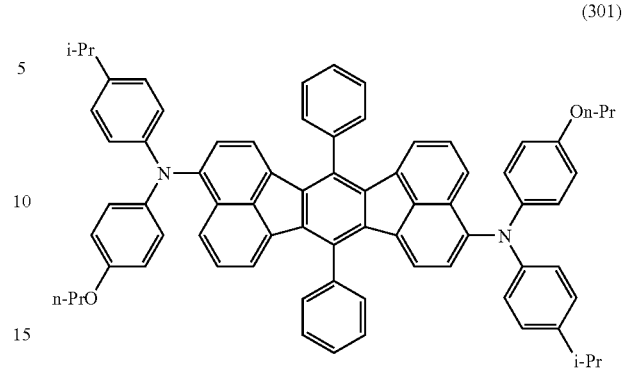
(301)
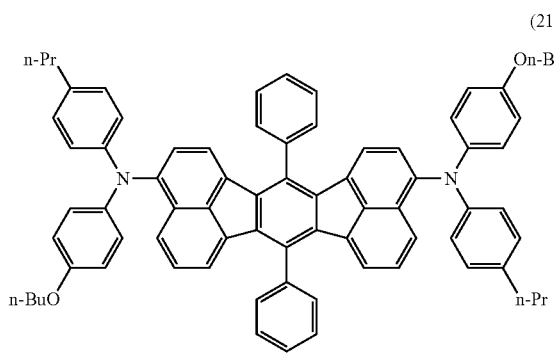
(212′)
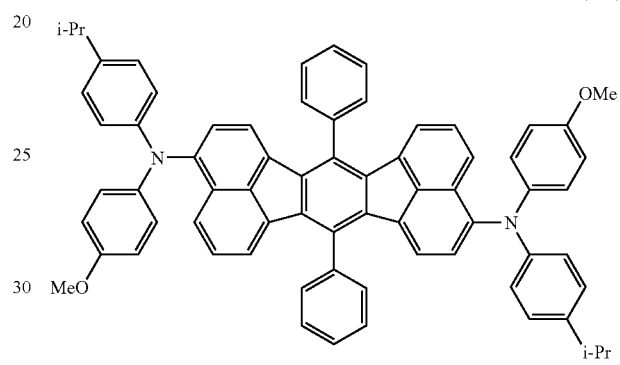
(302)
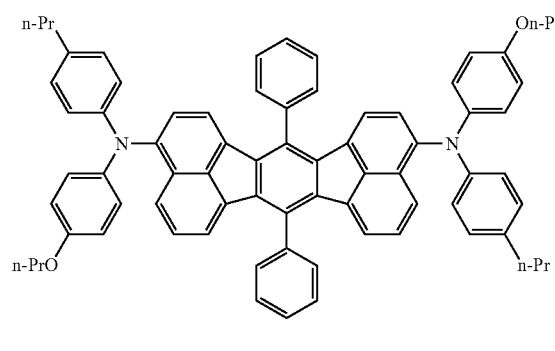
(213′)
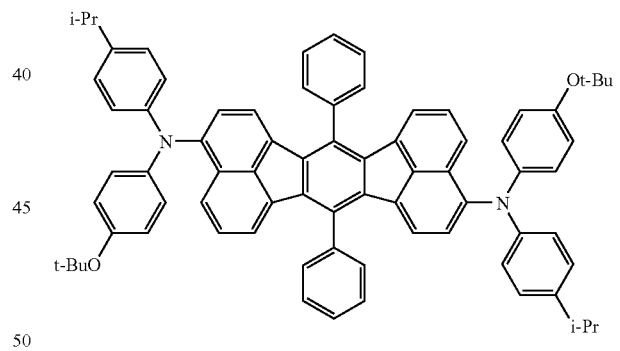
(303)
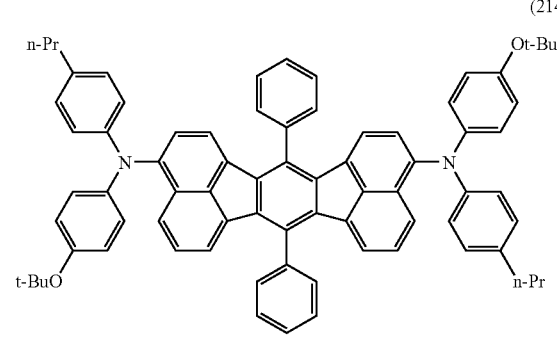
(214′)
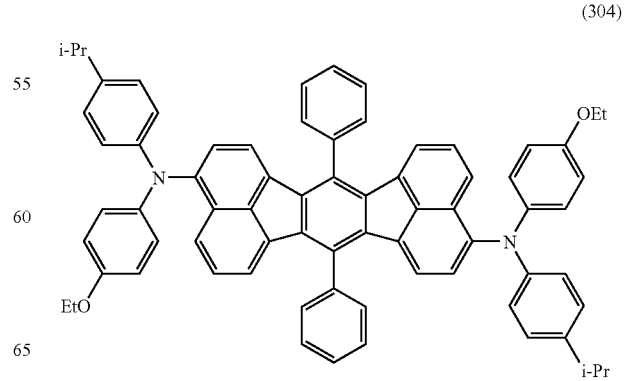
(304)

-continued
(305)
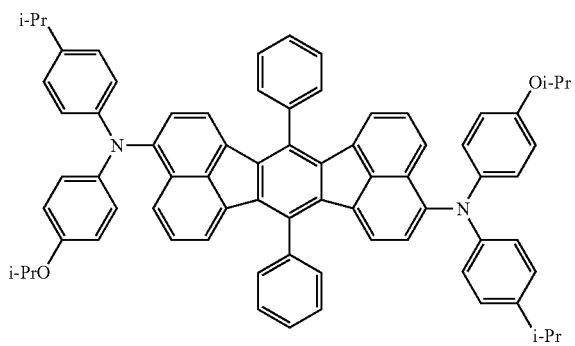
(306)
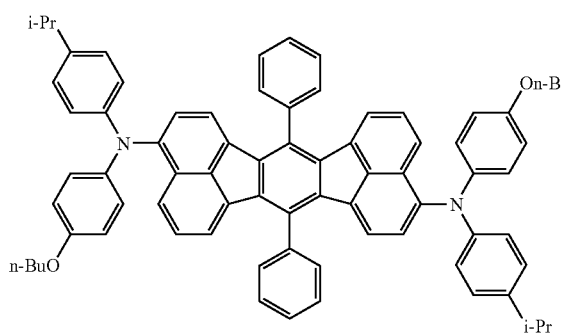
(307)
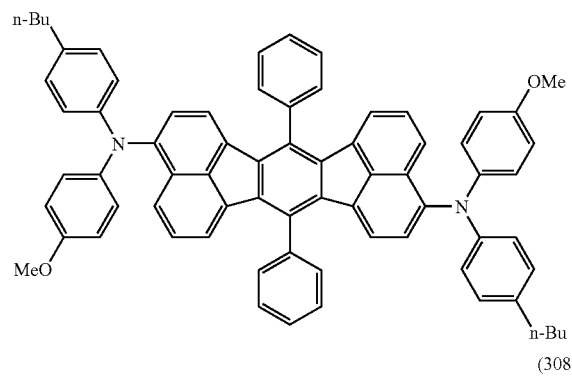
(308)
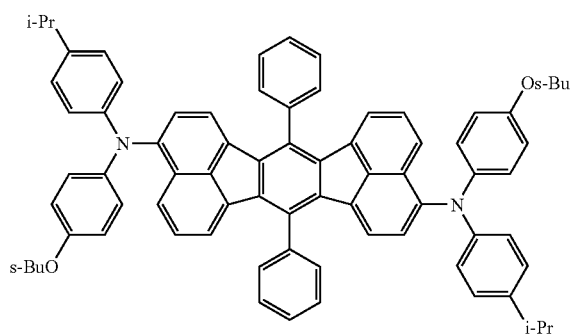
(309)
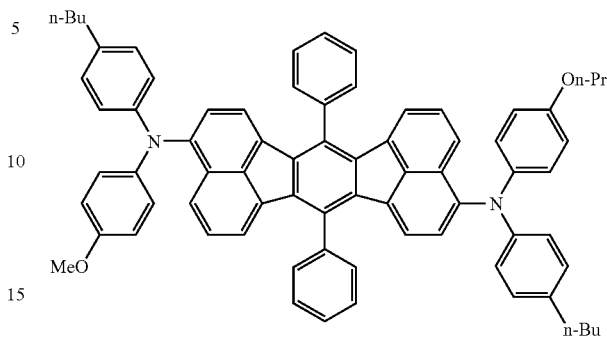
(310)
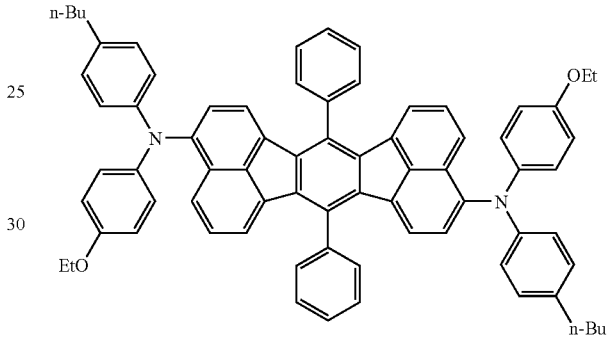
(311)
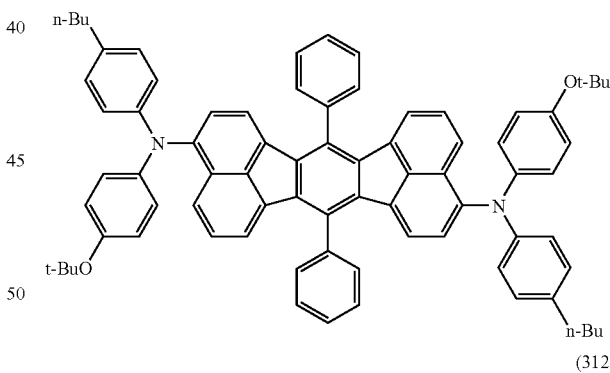
(312)
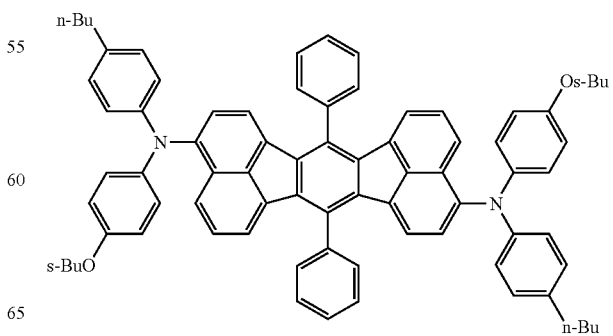

-continued
(313)
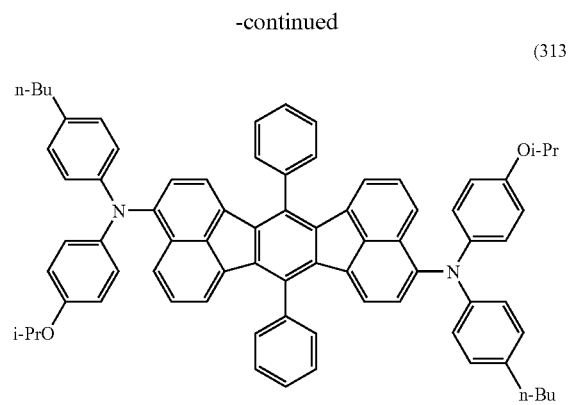
(314)
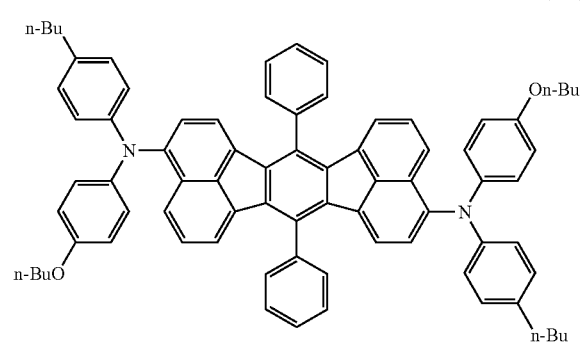
(301')
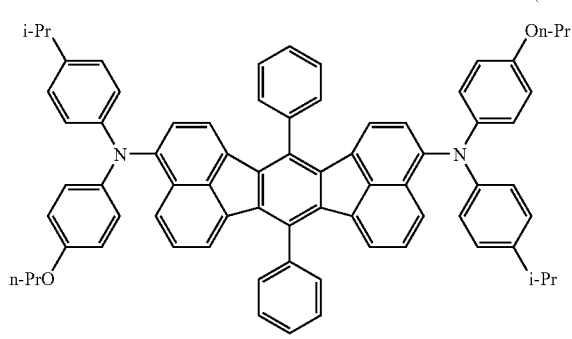
(302')
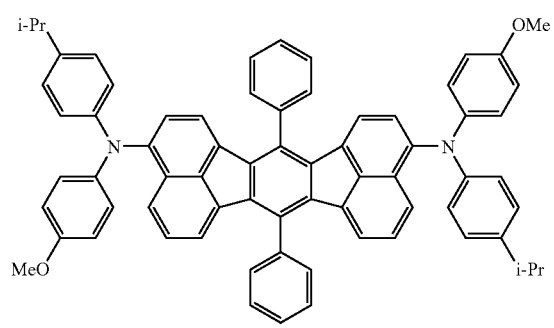
-continued
(303')
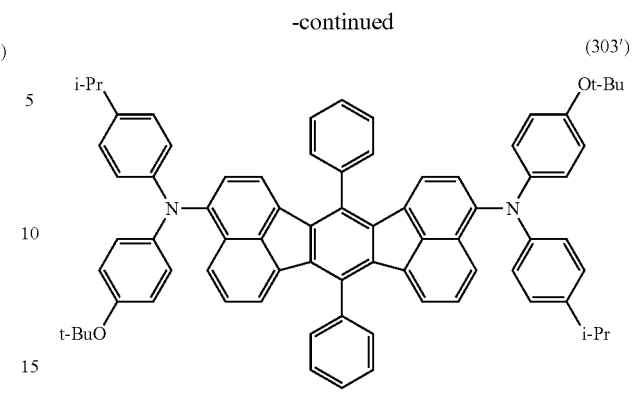
(304')
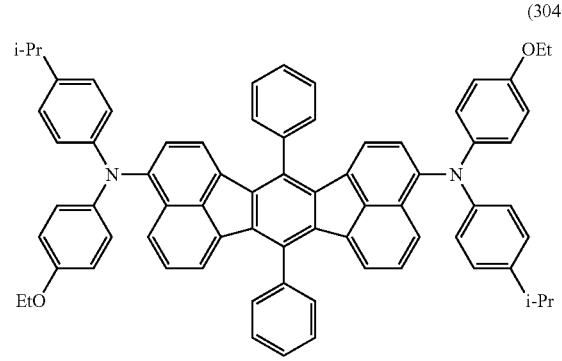
(305')
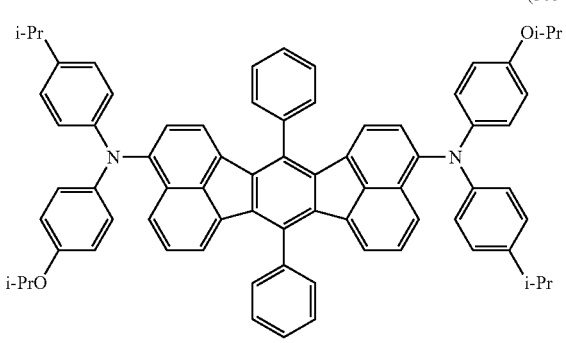
(306')
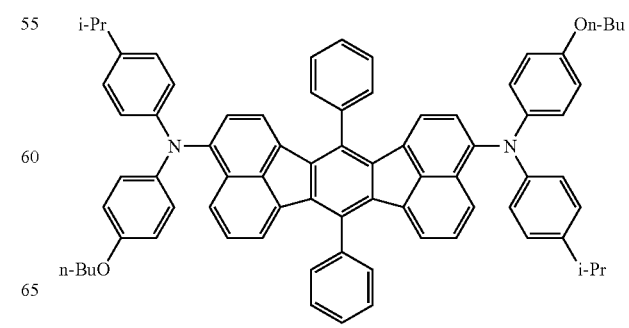

-continued
(307′)
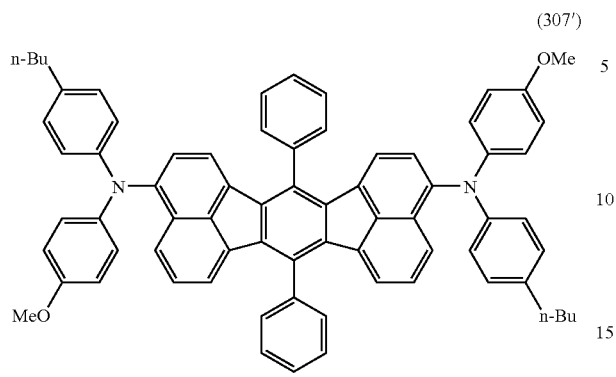
(311′)
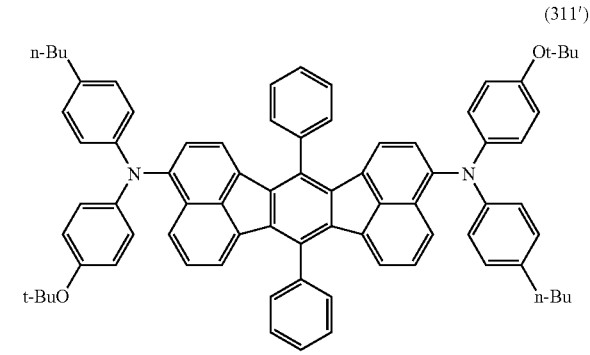
(308′)
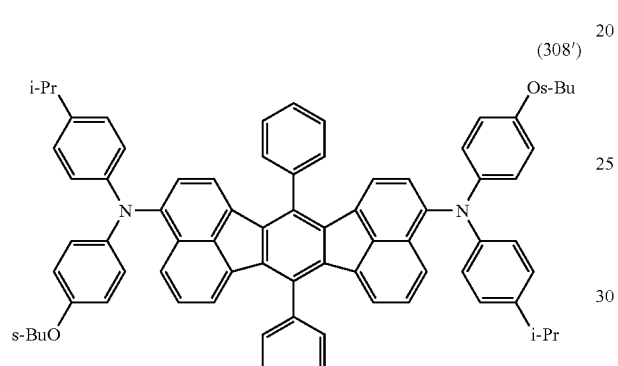
(312′)
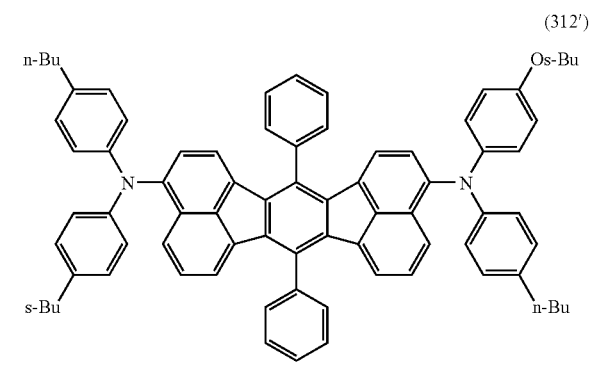
(309′)
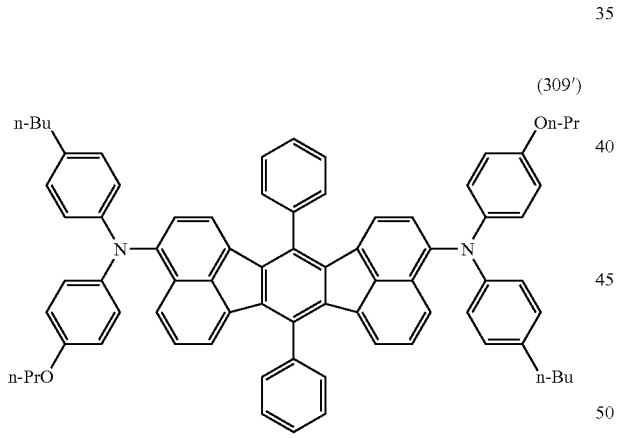
(313′)
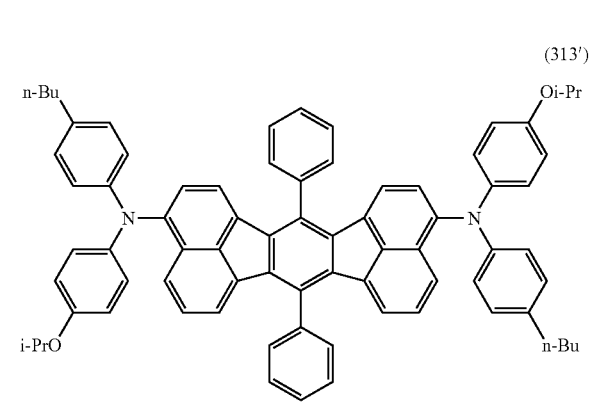
(310′)
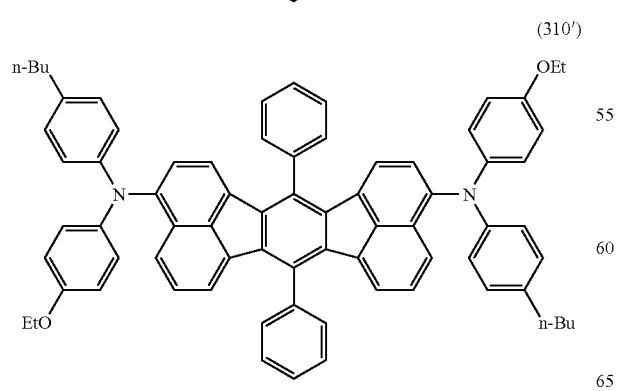
(314′)
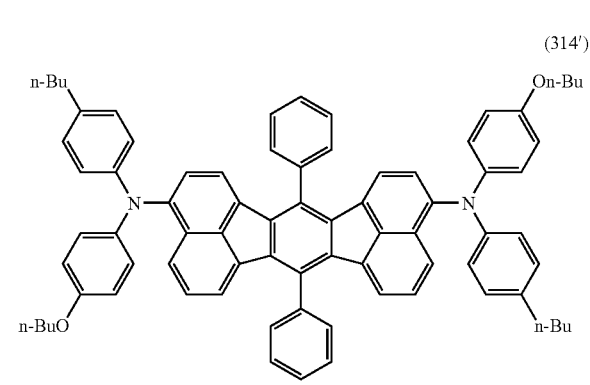

-continued
(401)
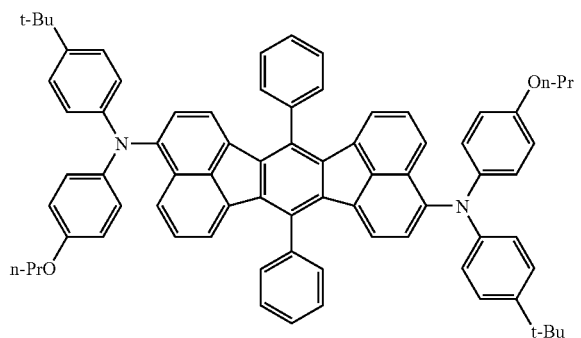
(402)
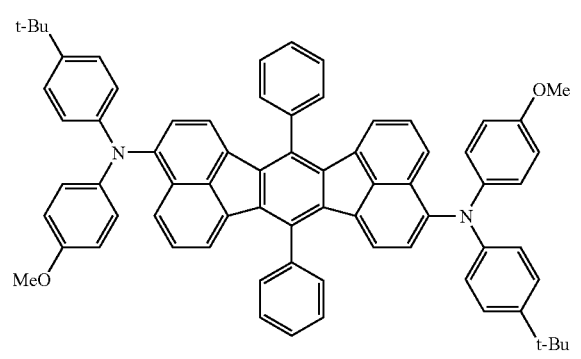
(403)
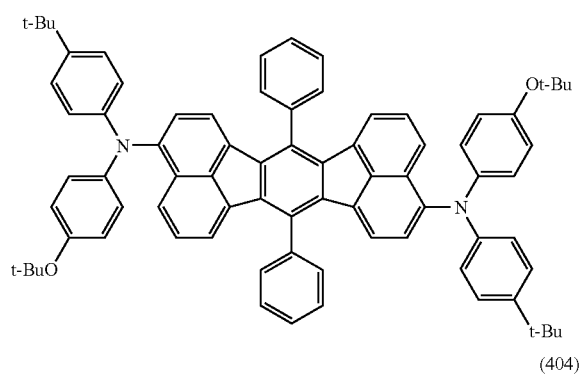
(404)
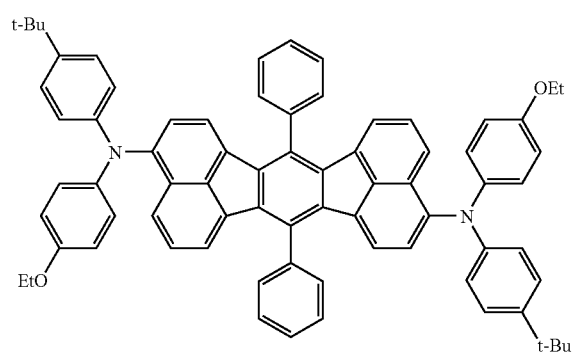
-continued
(405)
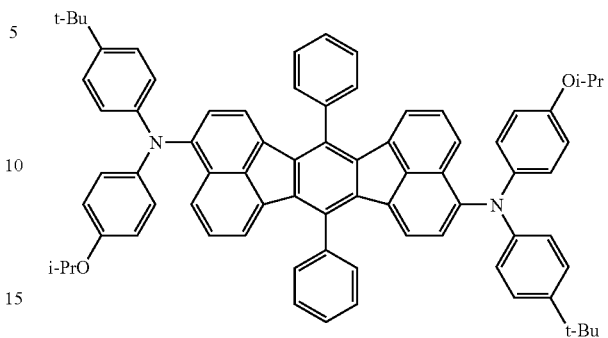
(406)
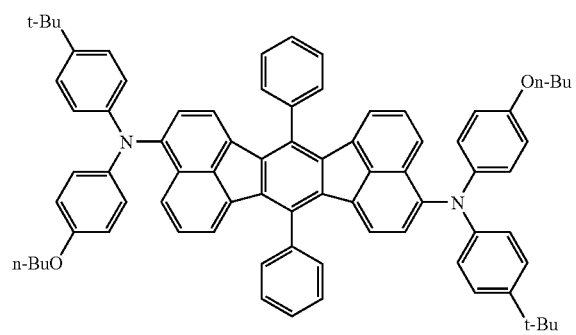
(407)
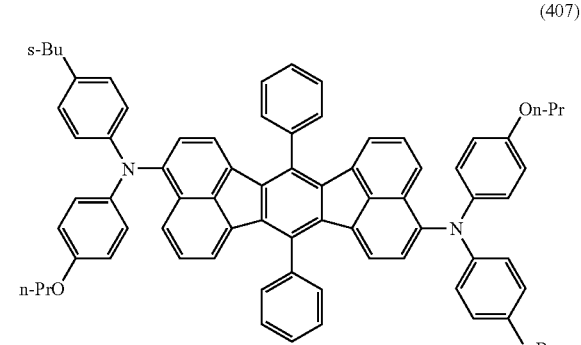
(408)
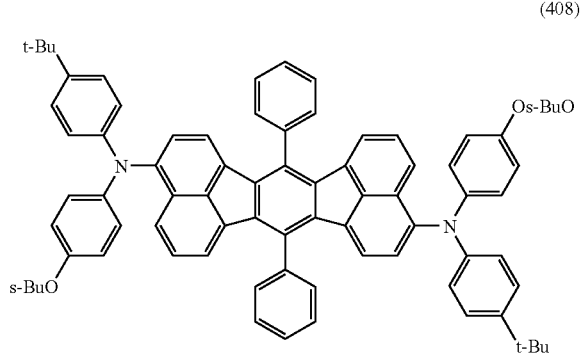

-continued
(409)
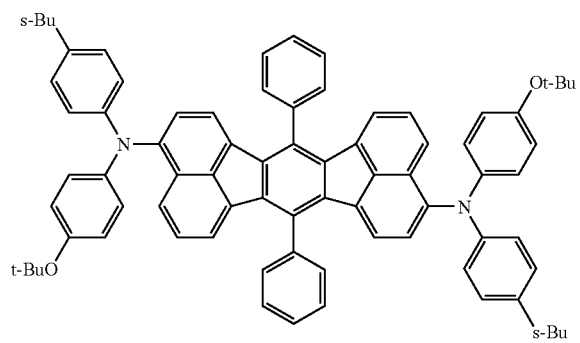
(410)
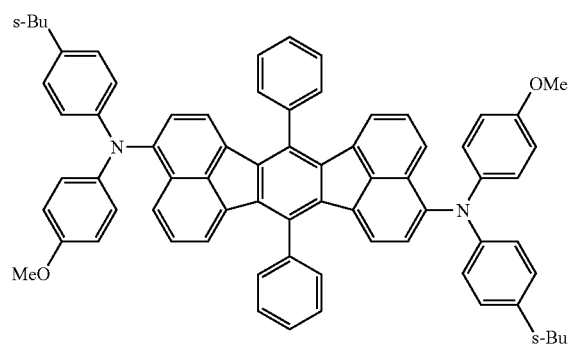
(411)
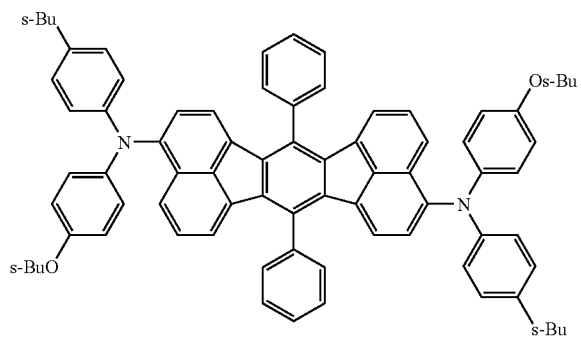
(412)
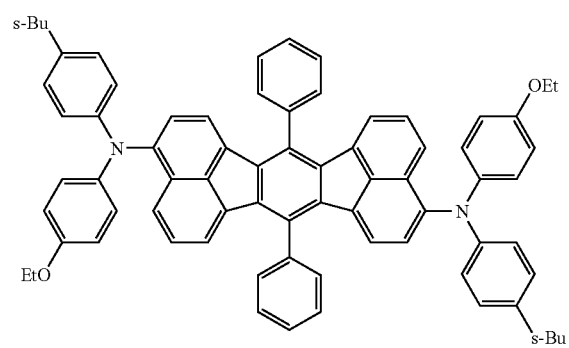
-continued
(413)
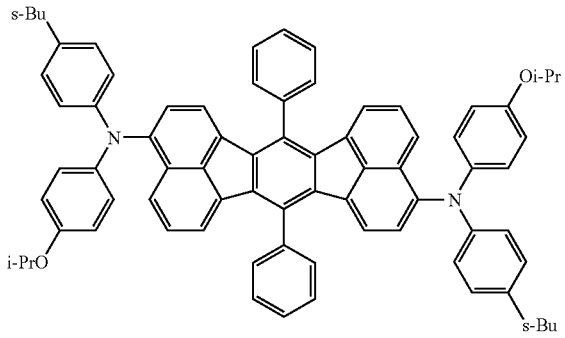
(414)
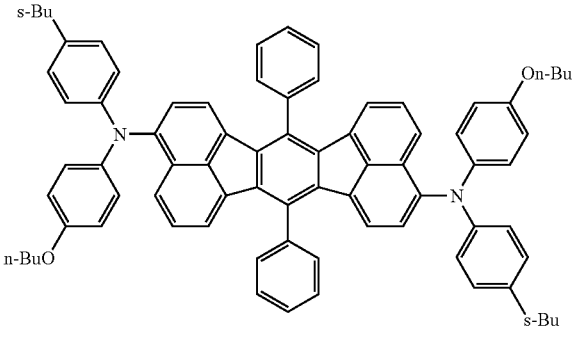
(401′)
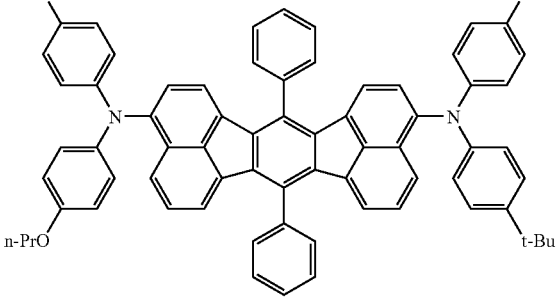
(402′)
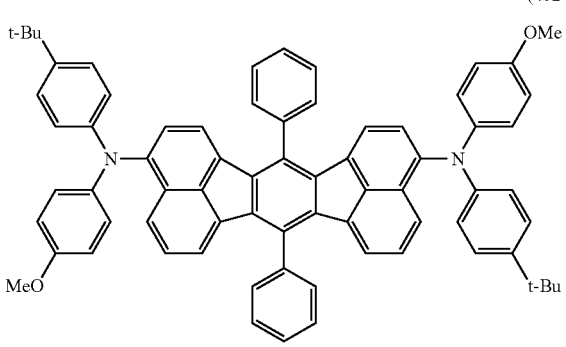

-continued
(403')
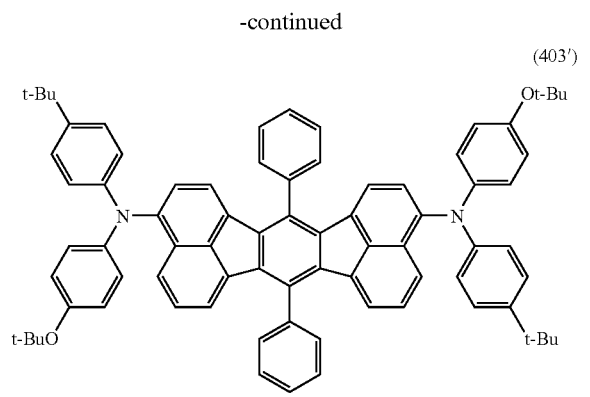
(404')
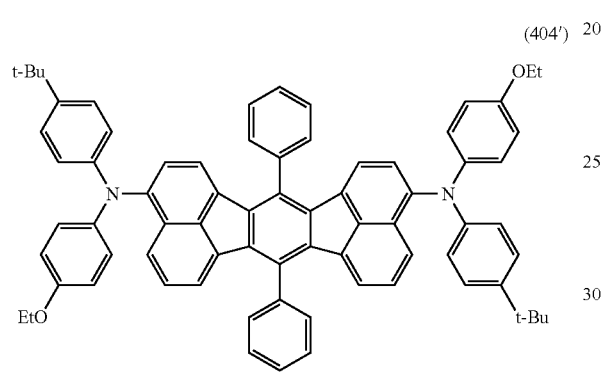
(405')
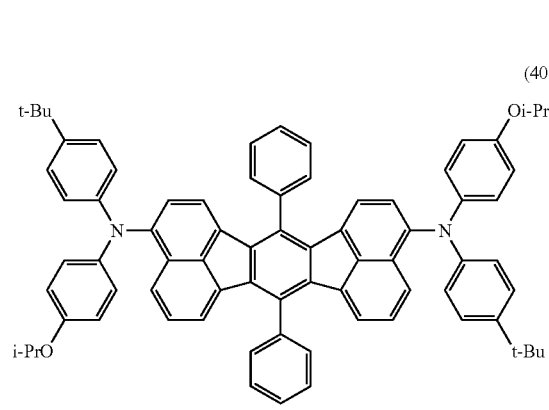
(406')
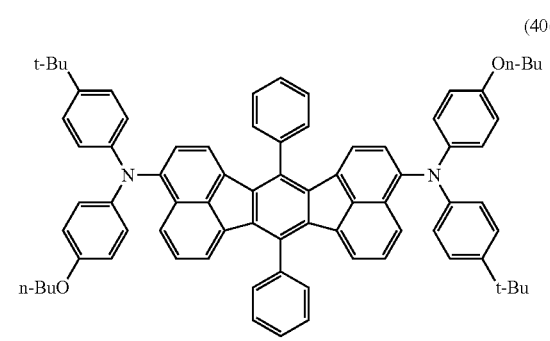
-continued
(407')
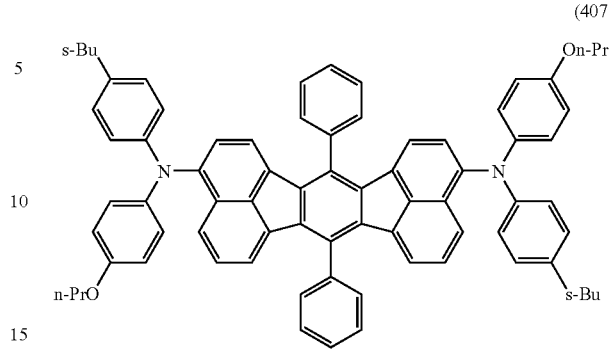
(408')
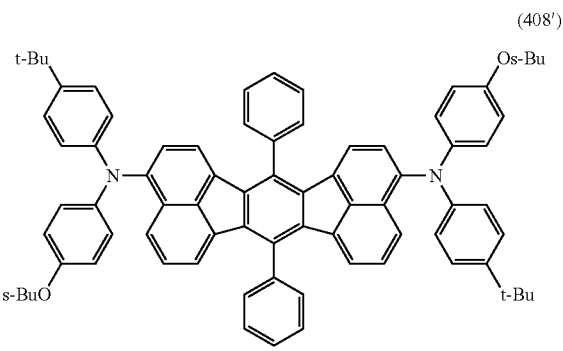
(409')
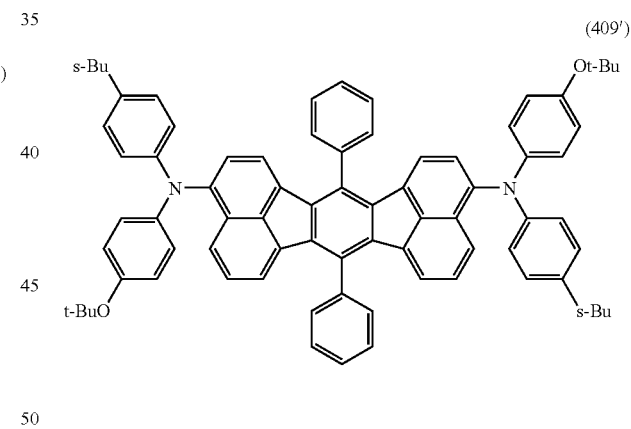
(410')
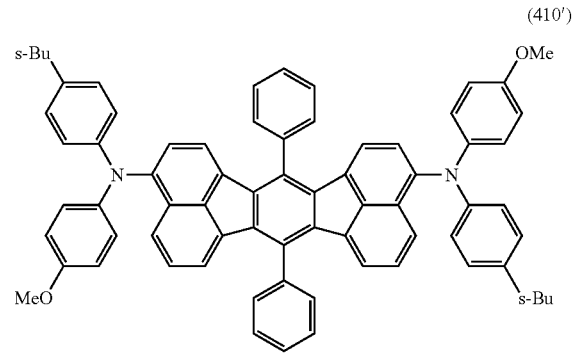

-continued
(411')
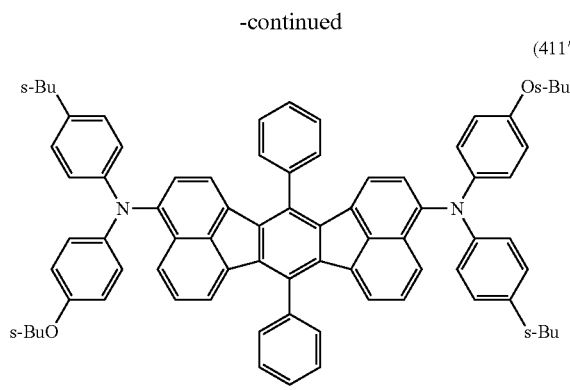
(501)
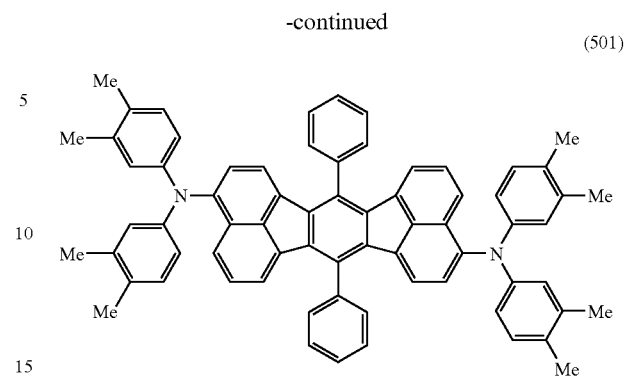
(412')
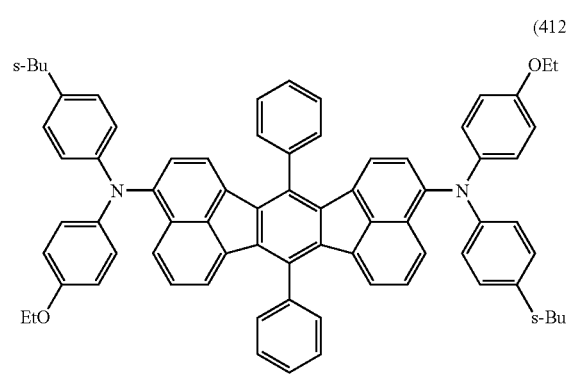
(502)
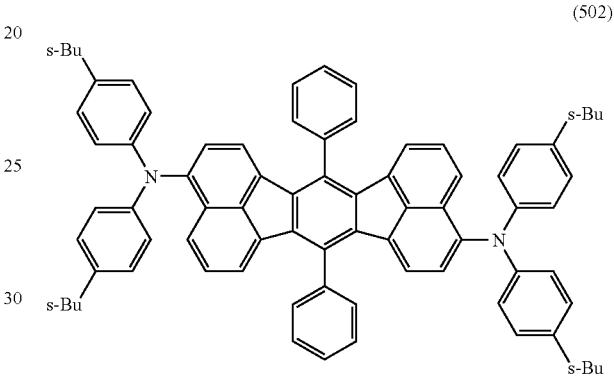
(413')
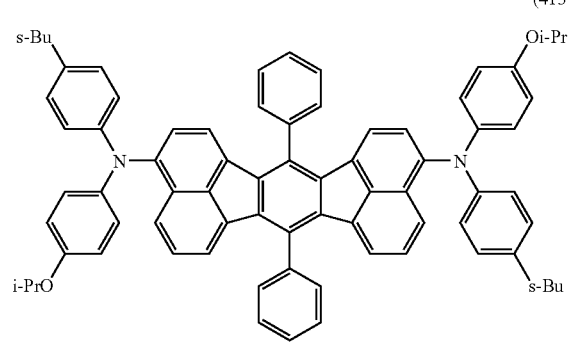
(503)
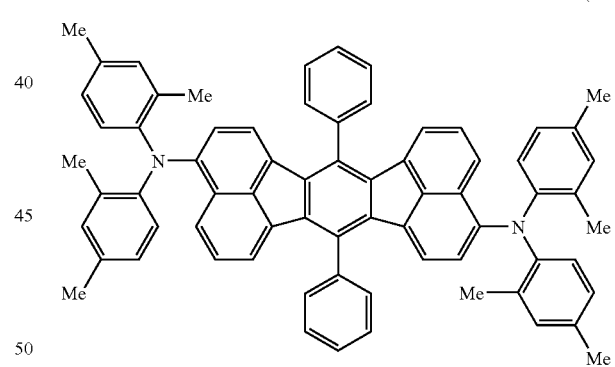
(414')
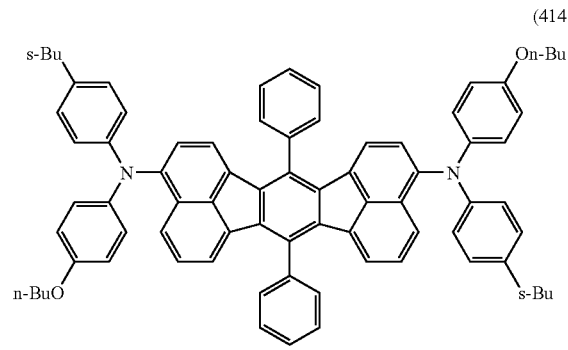
(504)
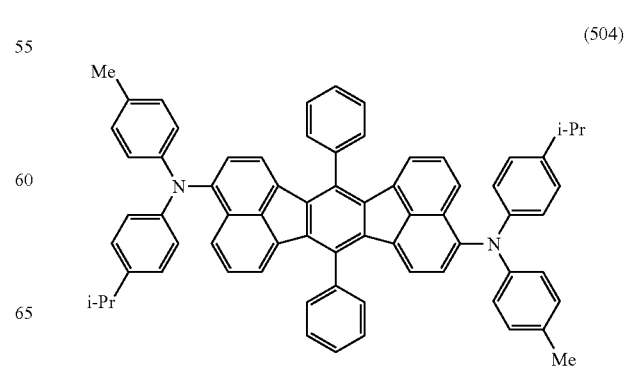

-continued
(505)
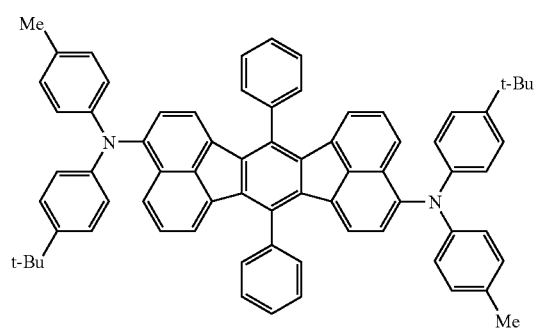
(506)
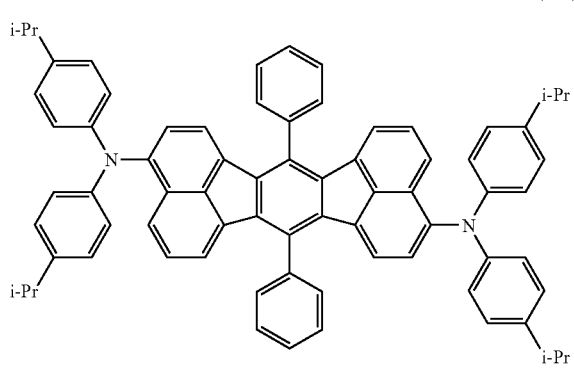
(507)
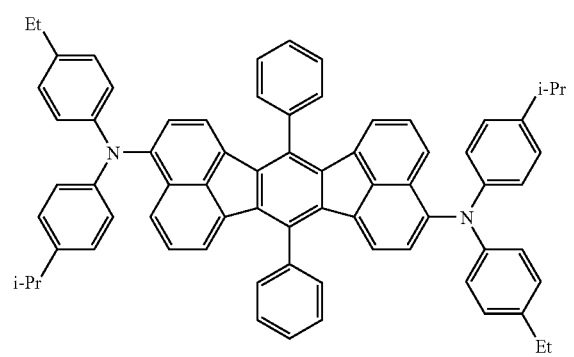
(508)
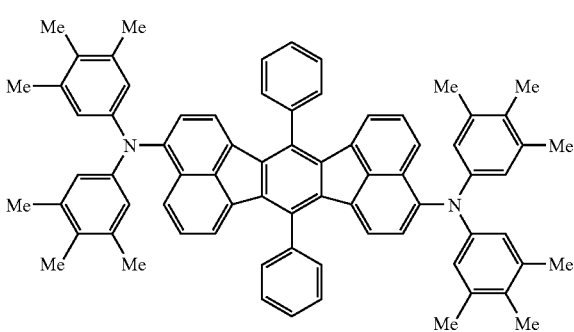
-continued
(509)
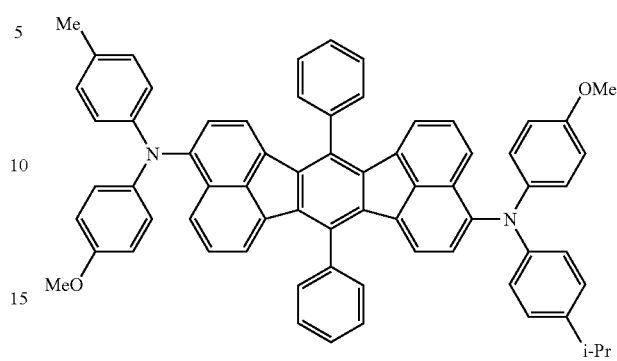
(510)
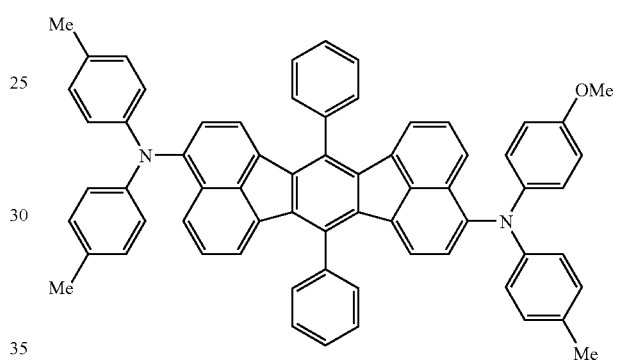
(511)
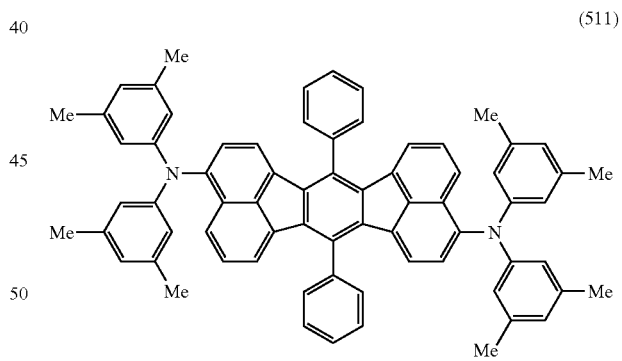
(512)
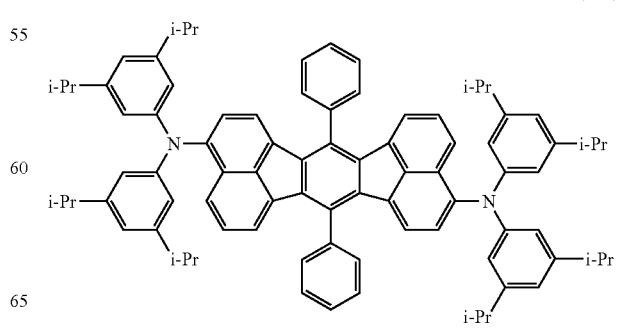

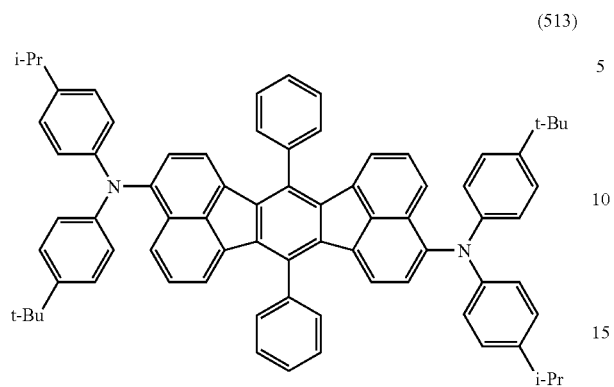 (513)
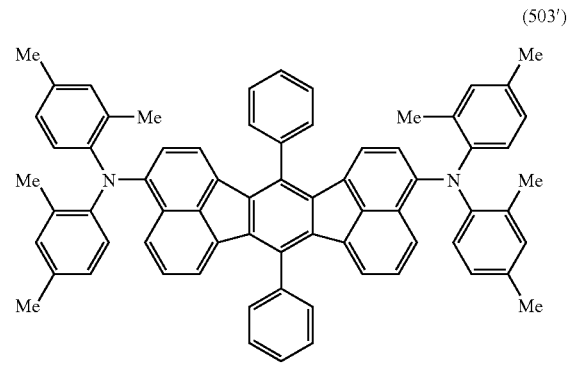 (503')
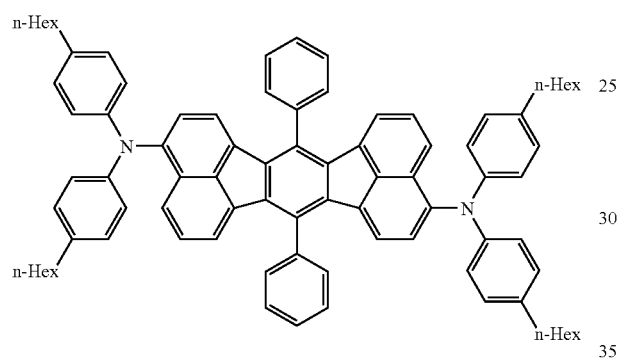 (514)
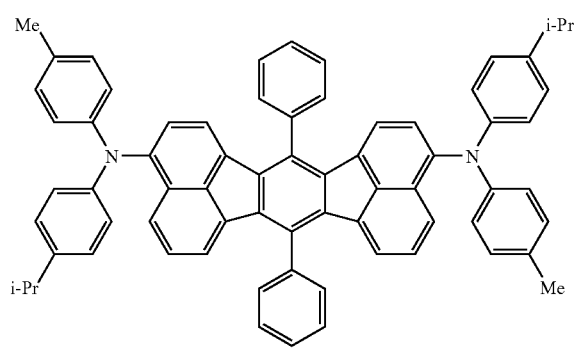 (504')
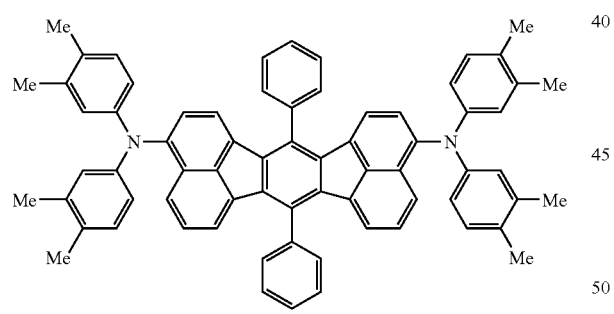 (501')
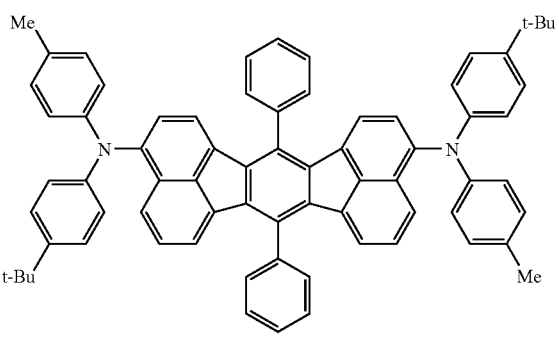 (505')
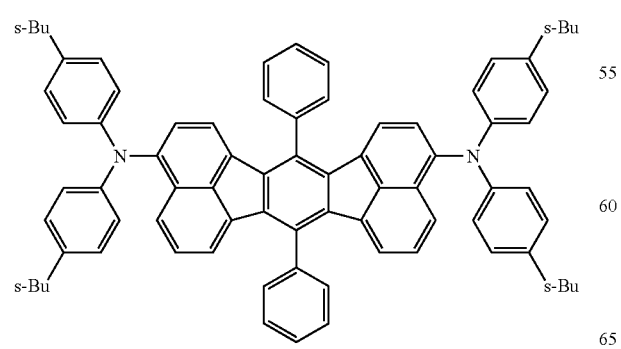 (502')
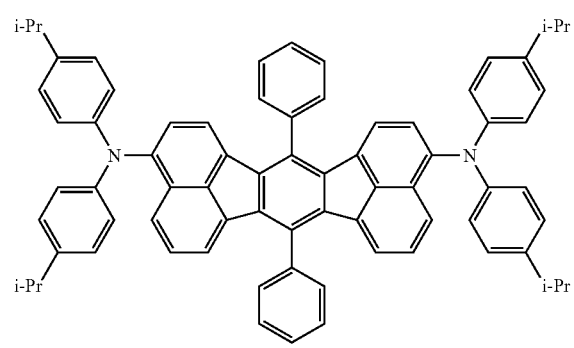 (506')

-continued
(507')
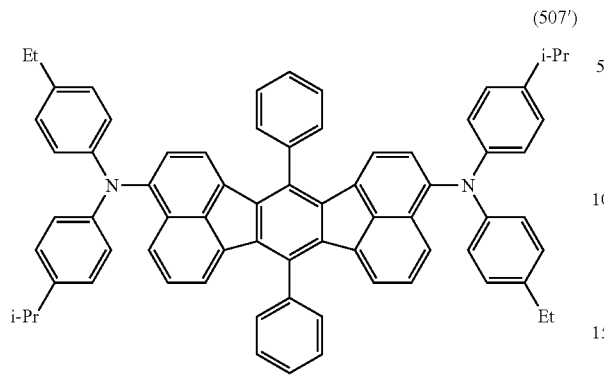
(511')
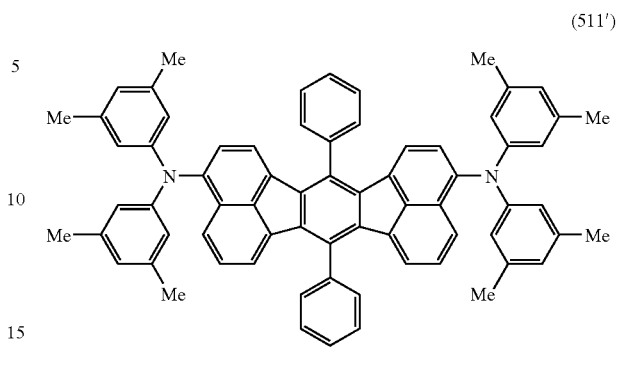
(508')
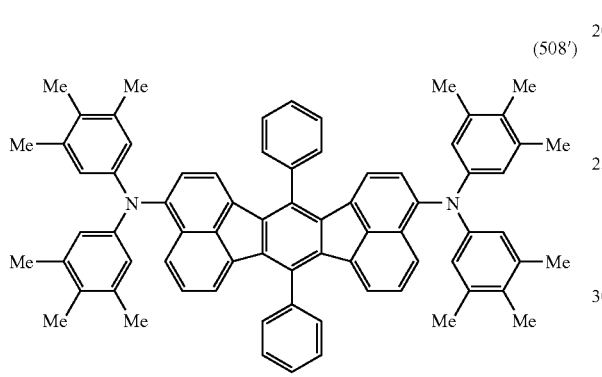
(512')
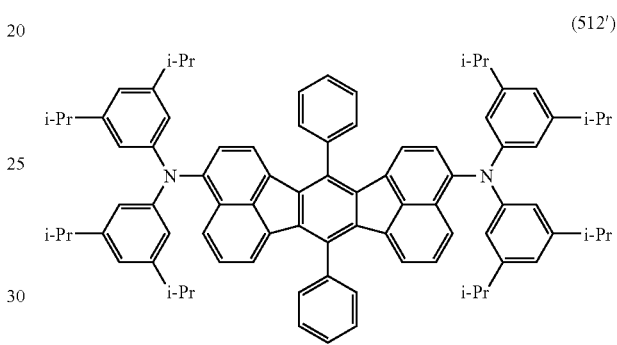
(509')
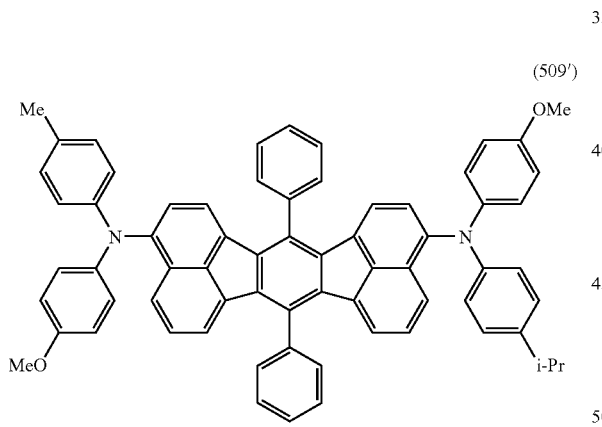
(513')
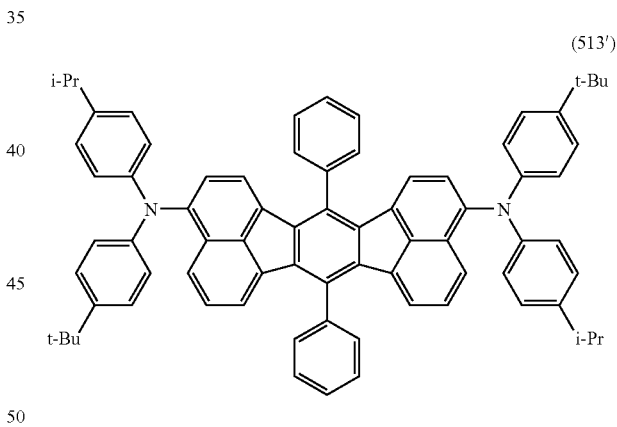
(510')
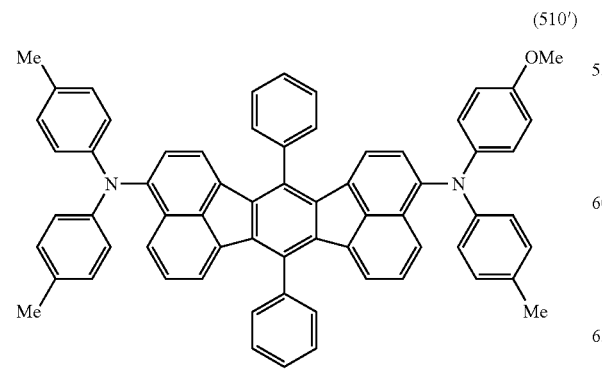
(514')
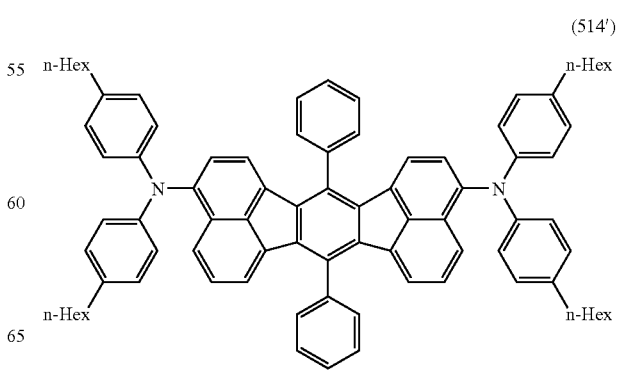

-continued
(601)
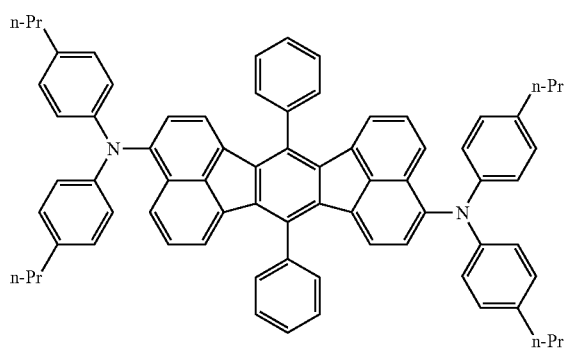
(602)
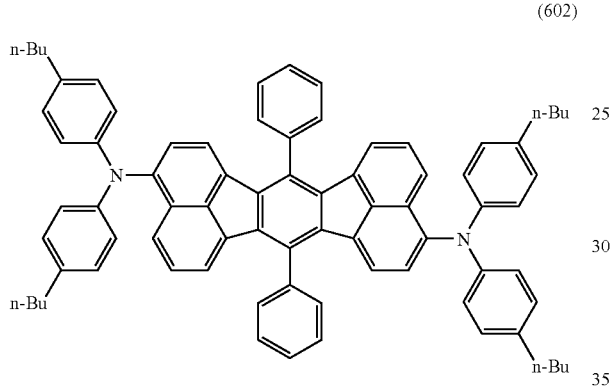
(603)
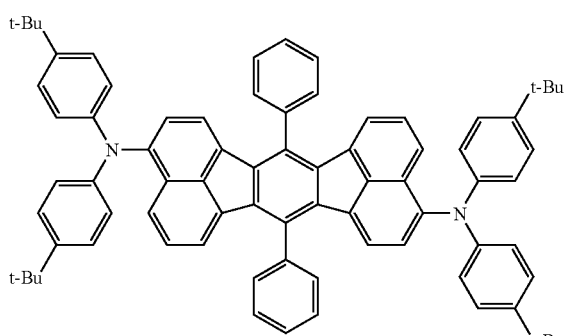
(604)
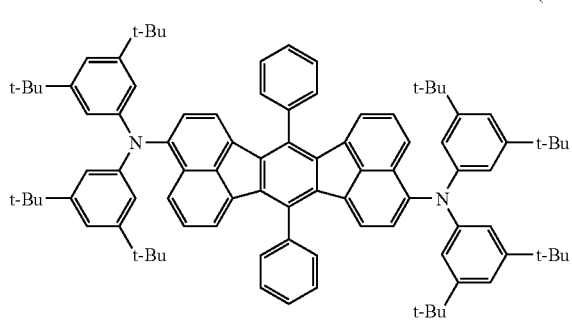
-continued
(605)
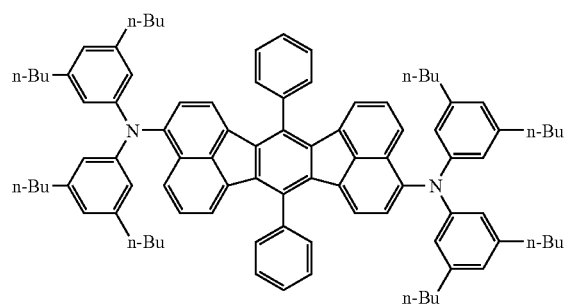
(606)
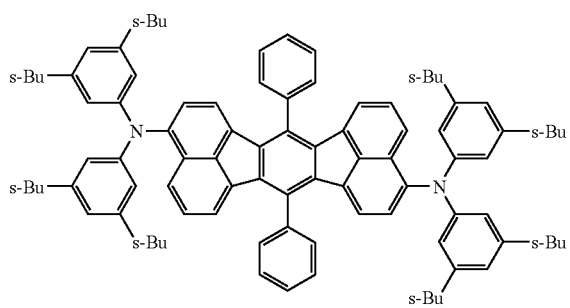
(607)
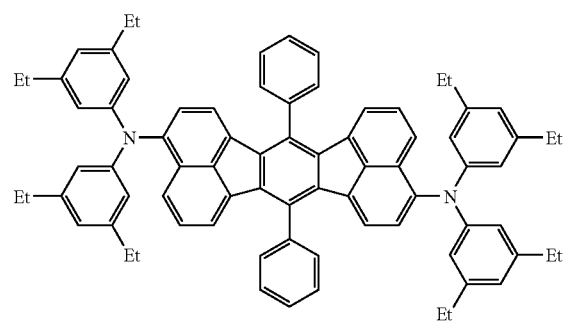
(608)
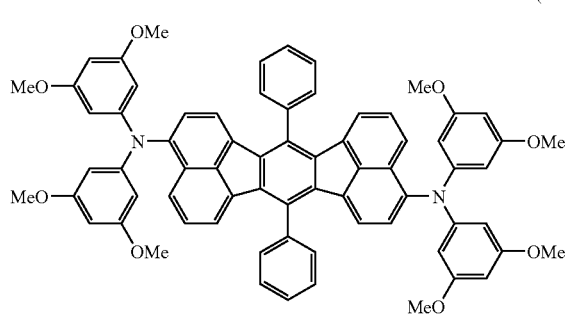

-continued
(609)
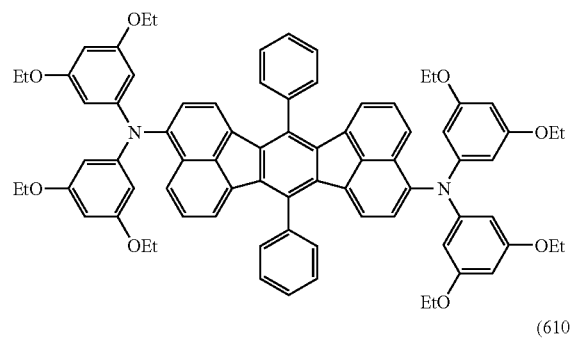
(610)
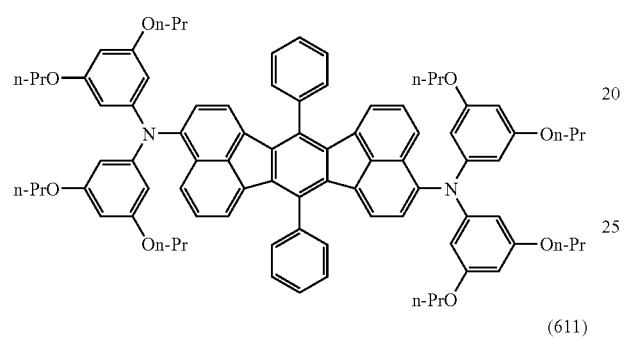
(611)
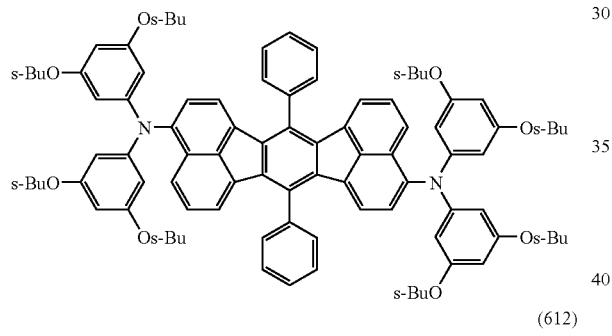
(612)
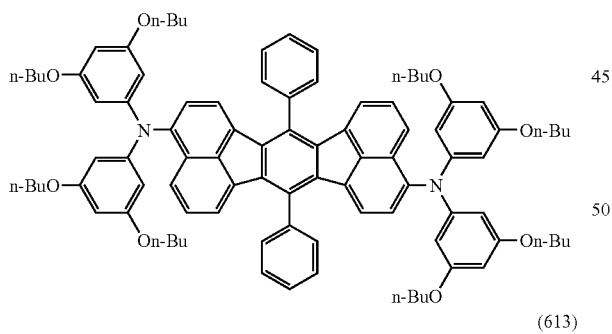
(613)
-continued
(614)
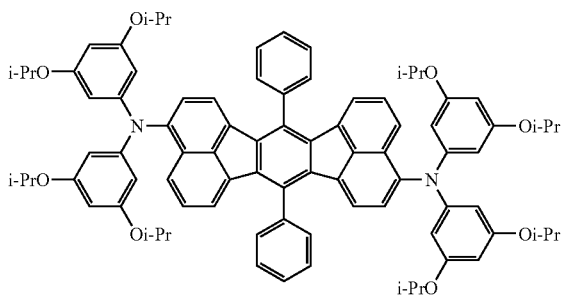
(601')
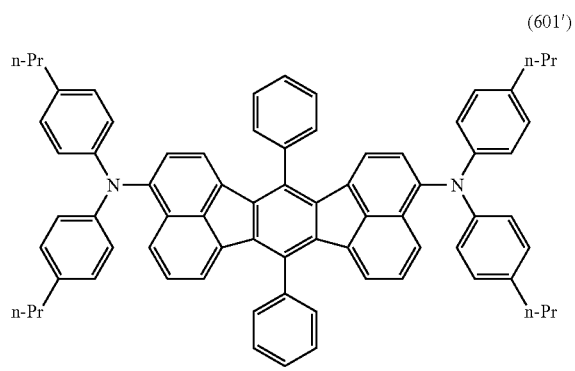
(602')
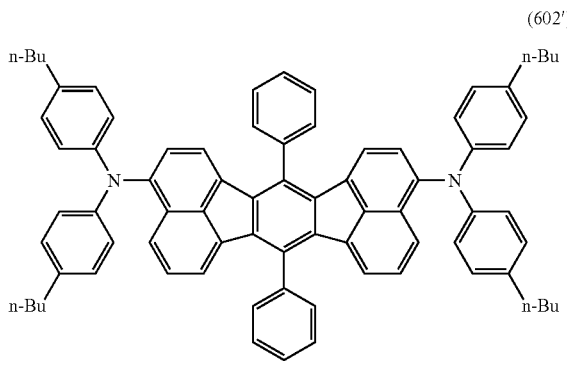
(603')
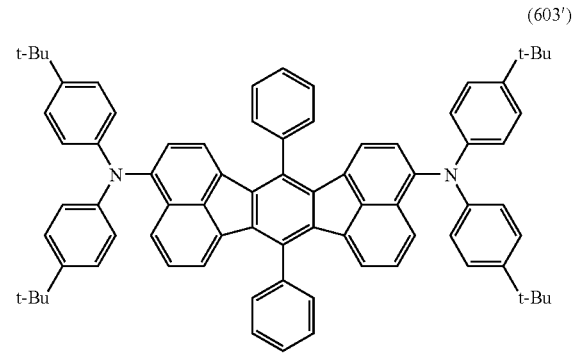

(604')
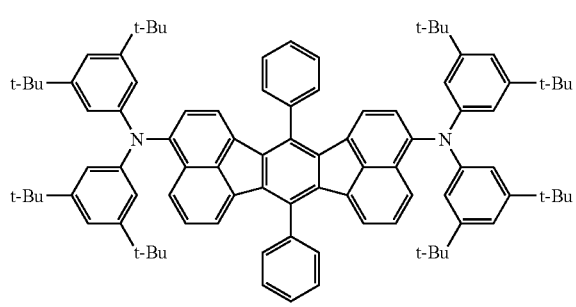
(605')
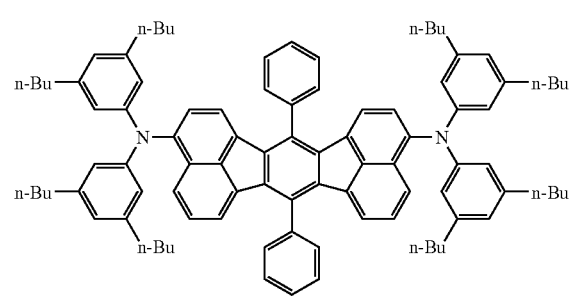
(606')
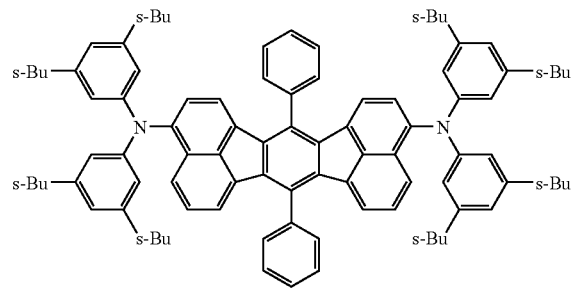
(607')
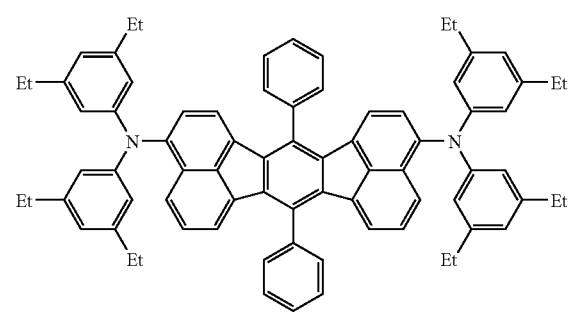
(608')
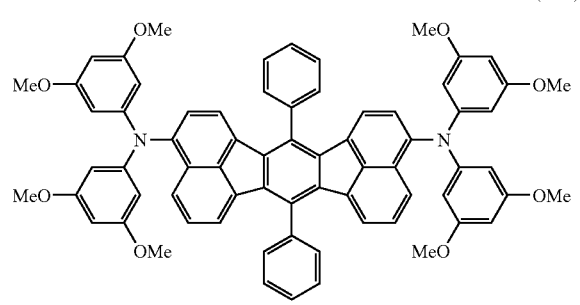
(609')
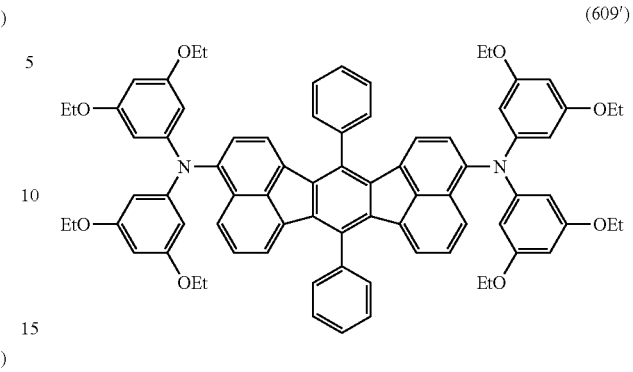
(610')
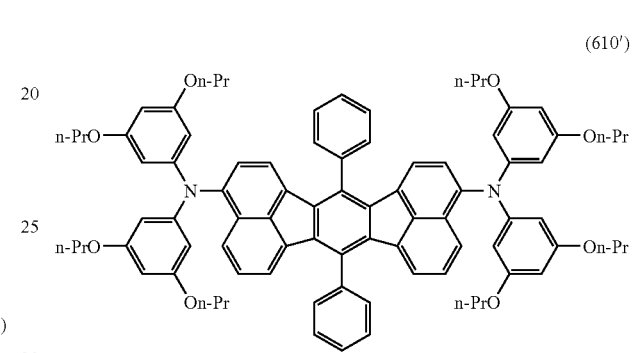
(611')
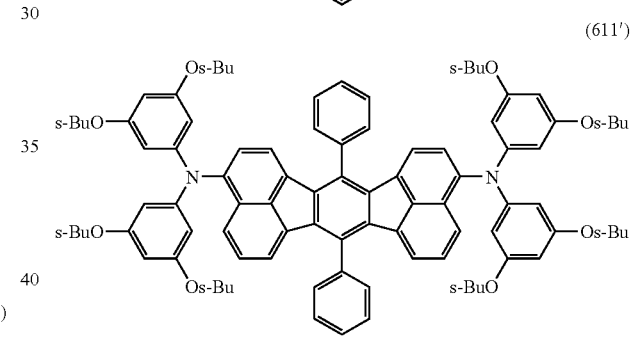
(612')
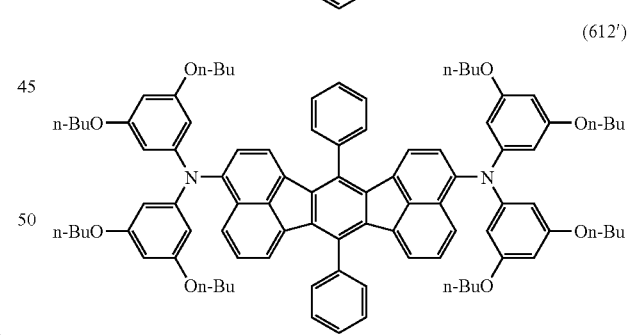
(613')
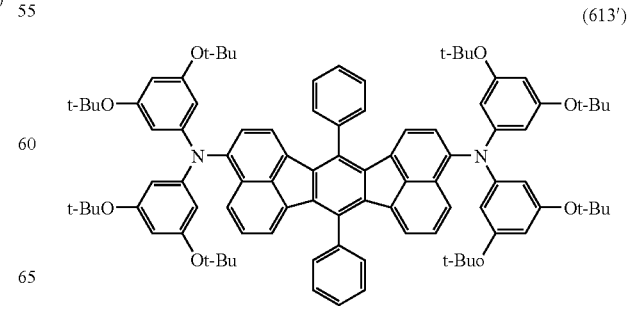

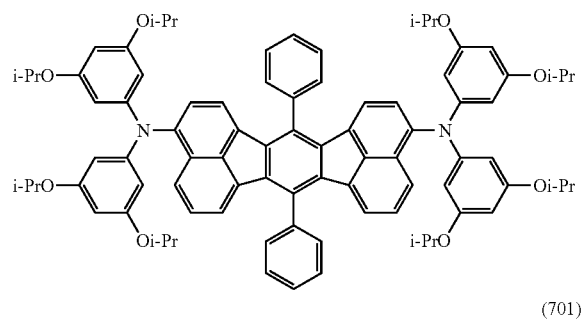
(614')
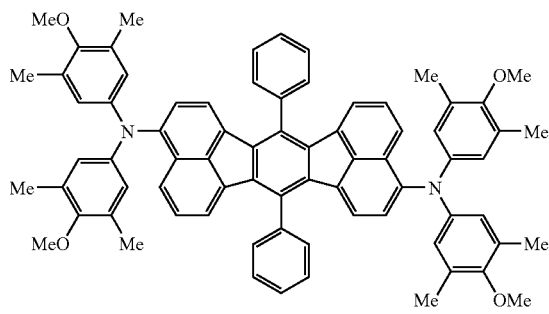
(705)
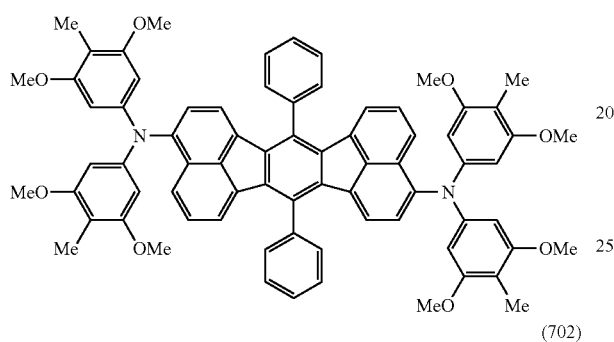
(701)
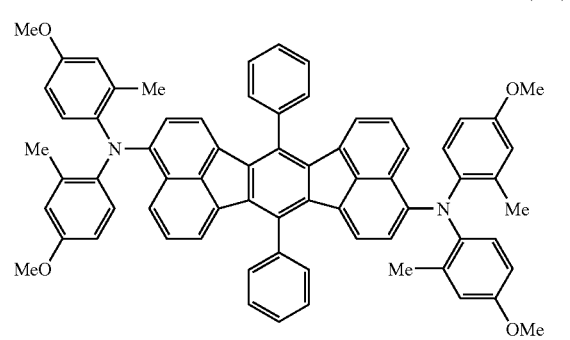
(706)
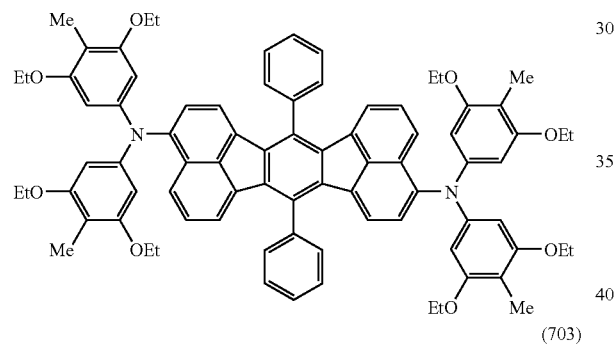
(702)
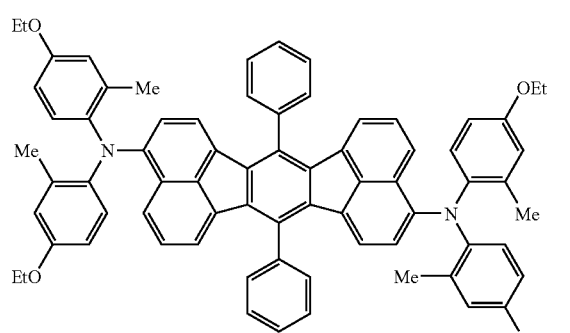
(707)
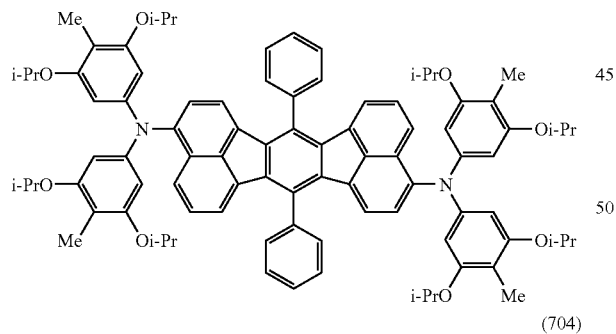
(703)
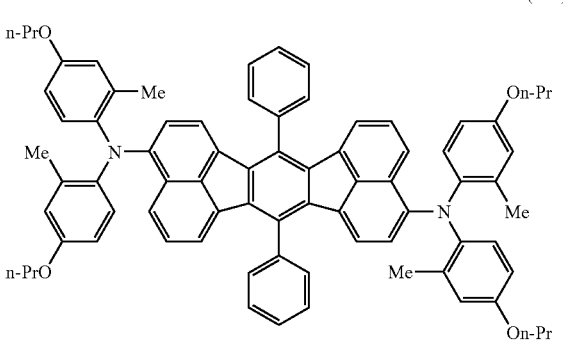
(708)
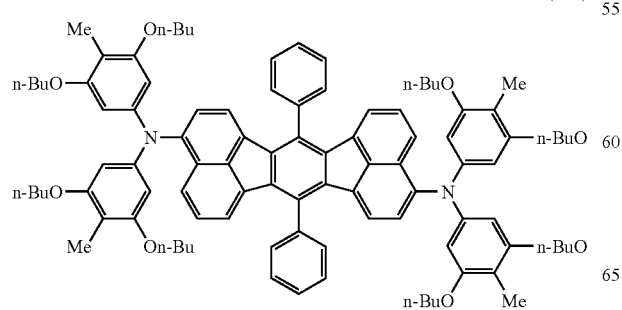
(704)

-continued
(709)
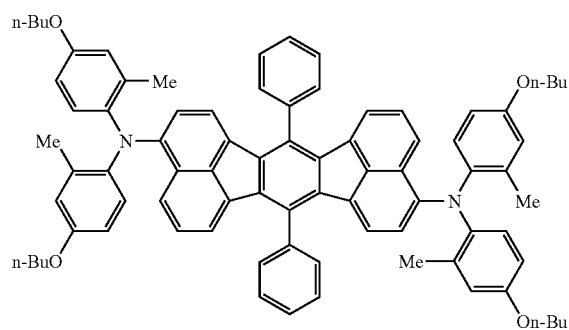
(710)
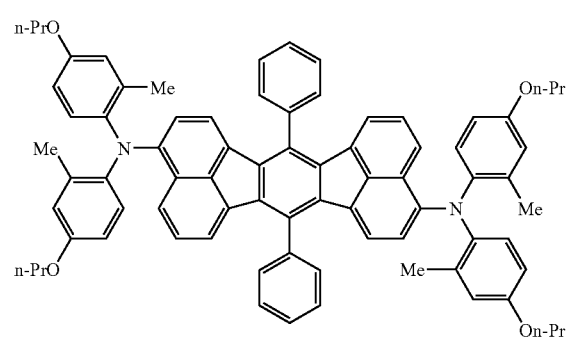
(711)
(712)
-continued
(713)
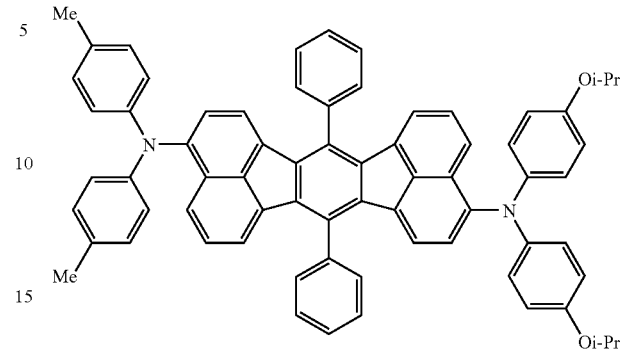
(714)
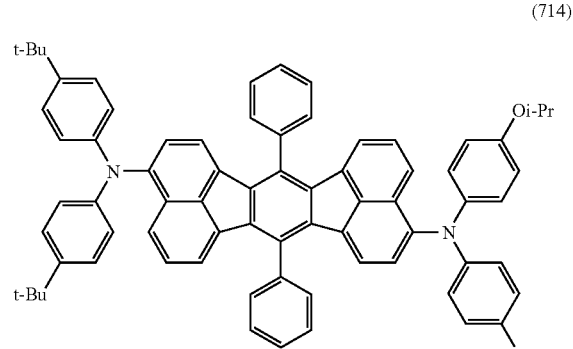
(701')
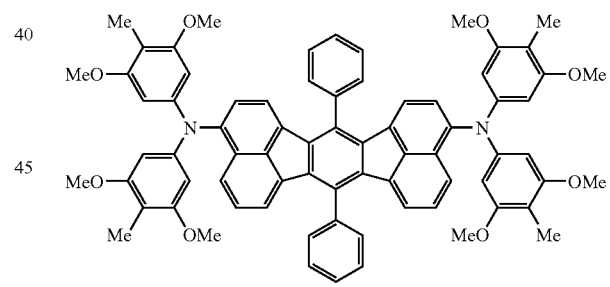
(702')
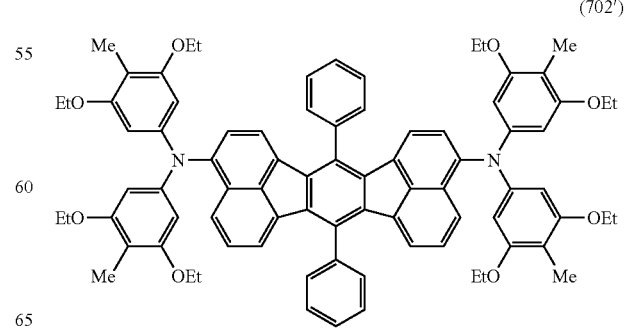

-continued
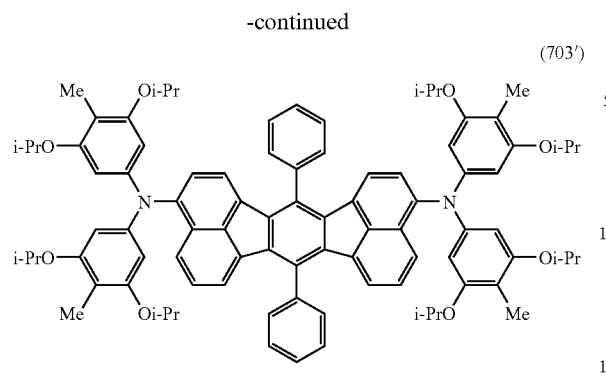
(703')
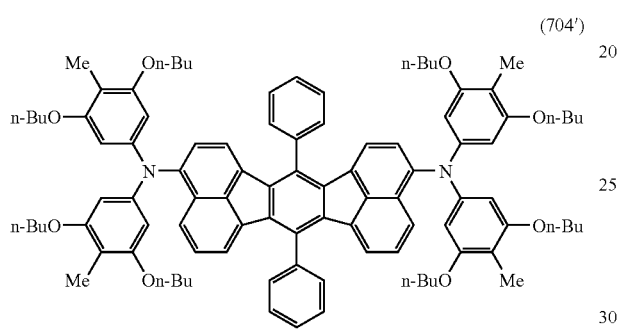
(704')
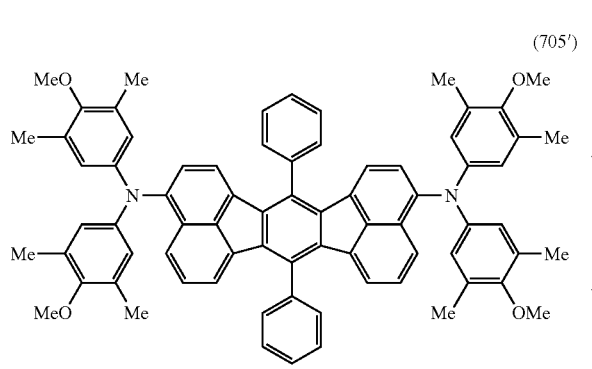
(705')
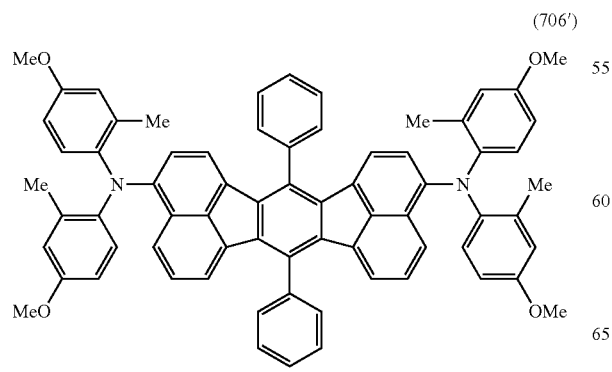
(706')
-continued
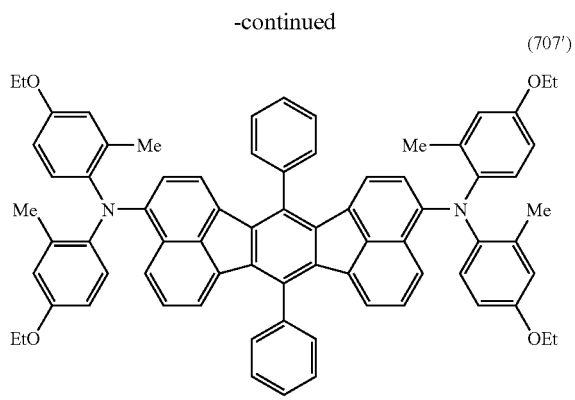
(707')
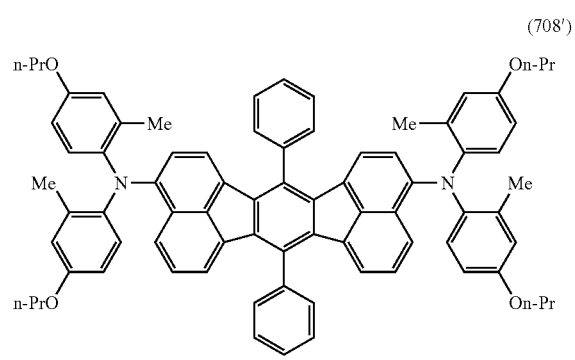
(708')
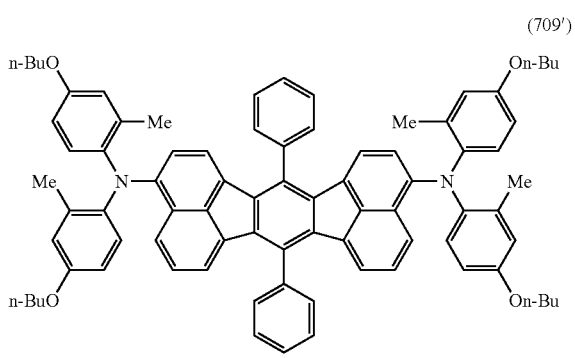
(709')
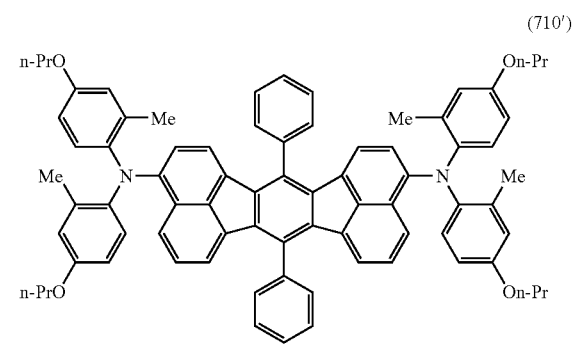
(710')

-continued

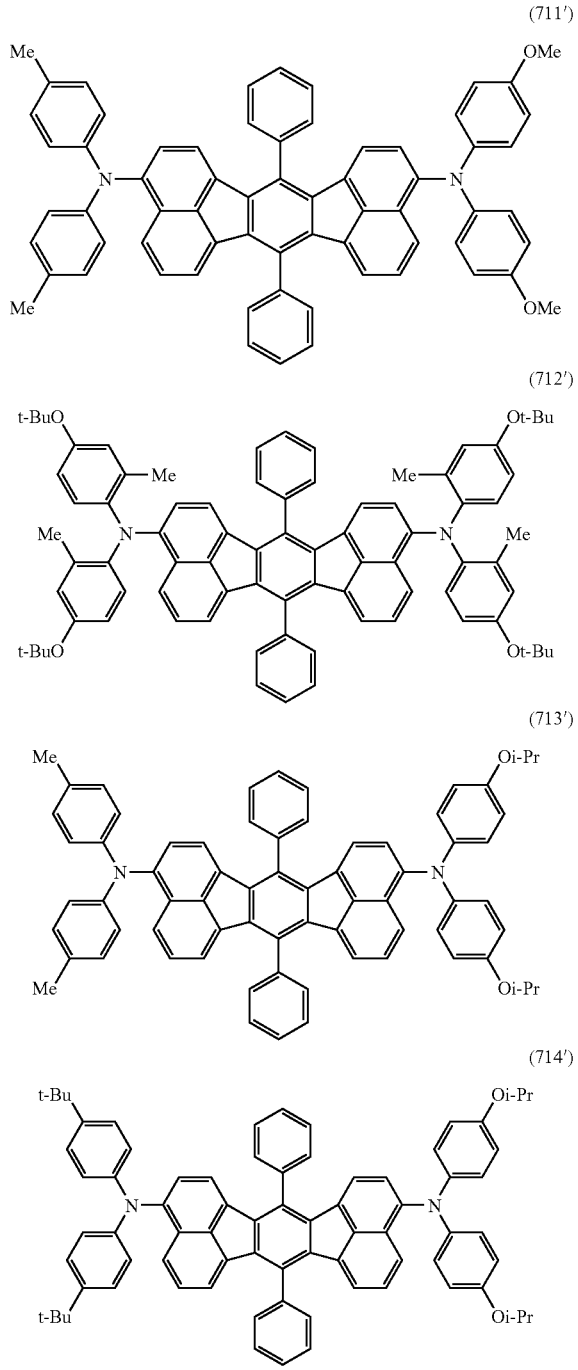

The organic EL device of the present invention comprises an organic compound layer comprising one or a plurality of layers formed between the anode and the cathode, and at least one of the layers in the organic compound layer comprises the aromatic compound represented by general formula (I) described above. When the device comprises a single layer, the layer is a light emitting layer formed between the anode and the cathode. The light emitting layer comprises a light emitting material and may further comprise a hole injection material for transporting holes injected from the anode to the light emitting material or an electron injection material for transporting electrons injected from the cathode to the light emitting material. It is preferable that the light emitting material exhibits a very excellent fluorescence quantum efficiency, has a great ability of transporting both holes and electrons and forms a uniform thin layer. Examples of the organic EL device of the multi-layer type include organic EL devices comprising a laminate having a multi-layer construction such as (the anode/the hole injection layer/the light emitting layer/the cathode), (the anode/the light emitting layer/the electron injection layer/the cathode) and (the anode/the hole injection layer/the light emitting layer/the electron injection layer/the cathode).

In the present invention, it is preferable that the organic compound layer is at least one of the hole transport layer and the light emitting layer.

It is preferable that the organic compound layer comprises 1 to 70% by weight of the aromatic compound represented by general formula (I). When the content is smaller than 1% by weight, the effect of the invention cannot be obtained. When the content exceeds 70% by weight, the durability and the efficiency of light emission tend to decrease.

Where necessary, the light emitting layer or the organic compound layer may further comprise conventional light emitting materials, other doping materials, hole injection materials and electron injection materials in combination with the compound represented by general formula (I) of the present invention. By using a multi-layer structure for the organic EL device, decreases in the luminance and the lifetime due to quenching can be prevented. Using other doping materials, the luminance of emitted light and the efficiency of light emission can be improved, and emission of red light or white light can be obtained. By using other doping materials contributing to the light emission of the phosphorescence in combination, the luminance of emitted light and the efficiency of light emission can be improved.

The hole injection layer, the light emitting layer and the electron injection layer may each have a multi-layer structure. When the hole injection layer has a multi-layer structure, the layer into which holes are injected from the electrode is called the hole injection layer, and the layer which receives holes from the hole injection layer and transports holes to the light emitting layer is called the hole transport layer. Similarly, when the electron injection layer has a multi-layer structure, the layer into which electron are injected from the electrode is called the electron injection layer, and the layer which receives electrons from the electron injection layer and transports electrons to the light emitting layer is called the electron transport layer. The layers are selected in accordance with energy levels of the material, heat resistance and adhesion with the organic thin film layers or the metal electrodes.

Examples of the light emitting material and the host material which can be used for the organic compound layer in combination with the compound represented by general formula (I) include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetrapheny-butadiene, coumarine, oxadiazole, aldazine, bis-benzoxazoline, bis-styryl, pyrazine, cyclopentadiene, metal complexes of quinoline, metal complexes of aminoquinoline, metal complexes of benzoquinoline, imines, diphenylethylene, vinylanthracene, diaminocarbazole, pyrane, thiopyrane, polymethine, melocyanine, oxinoid compounds chelated with imidazole, quinacridone, rubrene, stilbene-based derivatives and fluorescence pigments.

As the hole injection material, compounds which have the ability to transport holes, exhibits the excellent effect of receiving holes injected from the anode and the excellent effect of injecting holes to the light emitting layer or the light emitting material, prevents transfer of excitons formed in the light emitting layer to the electron injection layer or the electron injection material and has the excellent ability of forming a thin film, are preferable. Examples of the hole injection compound include phthalocyanine derivatives, naphthalocyanine derivatives, porphyrin derivatives, oxazoles, oxadiazoles, triazoles, imidazoles, imidazolones, imidazolethiones, pyrazolines, pyrazolones, tetrahydroimidazoles, oxazoles, oxadiazoles, hydrazones, acylhydrazones, polyarylalkanes, stilbene, butadiene, triphenylamine of the benzidine type, triphenylamine of the styrylamine type, triphenylamine of the diamine type, derivatives of the above compounds and macromolecular materials such as polyvinyl-carbazoles, polysilanes and electrically conductive macromolecules.

Among these hole injection materials, the more effective hole injection materials are aromatic tertiary amine derivatives and phthalocyanine derivatives. Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methyl-phenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane and oligomers and polymers having the skeleton structure of these aromatic tertiary amines. Examples of the phthalocyanine (Pc) derivative include phthalocyanine derivatives and naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O—GaPc.

As the electron injection material, compounds which have the ability to transport electrons, exhibits the excellent effect of receiving electrons injected from the anode and the excellent effect of injecting electrons to the light emitting layer or the light emitting material, prevents transfer of excitons formed in the light emitting layer to the hole injection layer and has the excellent ability of forming a thin film, are preferable. Examples of the electron injection compound include fluorenone, anthraquinodimethane, diphenoquinone, thiopyrane dioxide, oxazoles, oxadiazoles, triazoles, imidazoles, perylenetetracarboxylic acid, quinoxaline, fluorenylidenemethane, anthraquinodimethane, anthrone and derivatives of these compounds. The charge injection property can be improved by adding an electron accepting substance to the injecting hole material and an electron donating substance to the electron injection material.

Among these electron injection materials, the more effective electron injection materials are metal complex compounds and five-membered derivatives having nitrogen. Examples of the metal complex compound include 8-hydroxyquinolinatolithium, bis(8-hydroxy-quinolinato)zinc, bis(8-hydroxyquinolinato)copper, bis(8-hydroxy-quinolinato)manganese, tris(8-hydroxyquinolinato)aluminum, tris(2-methyl-8-hydroxyquinolinato)aluminum, tris(8-hydroxyquinolinato)-gallium, bis(10-hydroxybenzo[h]quinolinato)beryllium, bis(10-hydroxy-benzo[h]-quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum and bis(2-methyl-8-quinolinato)-(2-naphtholato)gallium.

As the five-membered derivative having nitrogen, oxazoles, thiazoles, oxadiazoles, thiadiazoles, triazoles and derivatives of these compounds are preferable. Examples of the five-membered derivative having nitrogen include 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,5-oxadiazole, 2,5-bis(1-naphthyl)-1,3,4-oxadiazole, 1,4-bis[2-(5-phenyloxadiazolyl)]benzene, 1,4-bis[2-(5-phenyl-oxadiazolyl)-4-tert-butylbenzene], 2-(4'-tert-butyl-phenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butyl-phenyl)-5-(4"-biphenyl)-1,3,4-triazole, 2,5-bis(1-naphthyl)-1,3,4-triazole and 1,4-bis[2-(5-phenyl-triazolyl)]benzene.

The organic EL device of the present invention may comprise an inorganic compound layer between the electrode and the above organic compound layer. Examples of the preferable inorganic compound used for the inorganic compound layer include various types of oxides, nitrides and oxide nitrides such as alkali metal oxides, alkaline earth metal oxides, rare earth oxides, alkali metal halides, alkaline earth metal halides, rare earth halides, $SiO_x$, $AlO_x$, $SiN_x$, SiON, AlON, $GeO_x$, $LiO_x$, LiON, $TiO_x$, TiON, $TaO_x$, TaON, $TaN_x$ and C. In particular, as the component contacting the anode, $SiO_x$, $AlO_x$, $SiN_x$, SiON, AlON, $GeO_x$ and C are preferable since a stable interface layer of injection is formed. As the component contacting the cathode, LiF, $MgF_2$, $CaF_2$, $MgF_2$ and NaF are preferable.

In the organic EL device of the present invention, it is possible that a protective layer is formed on the surface of the device or the entire device is covered with a silicone oil or a resin so that stability to the temperature, the humidity and the atmosphere is improved.

As the electrically conductive material used for the anode of the organic EL device of the present invention, a material having a work function greater than 4 eV is suitable, and carbon, aluminum, vanadium, iron, cobalt, nickel, tungsten, silver, gold, platinum, palladium, alloys of these metals, metal oxides such as tin oxides and indium oxide used for ITO substrates and NESA substrates and organic electrically conductive resins such as polythiophene and polypyrrol are used. As the electrically conductive material used for the cathode, a material having a work function smaller than 4 eV is suitable, and magnesium, calcium, tin, lead, titanium, yttrium, lithium, ruthenium, manganese, aluminum and alloys of these metals are used. However, the electrically conductive material used for the electrodes is not limited to these materials. Examples of the alloy include magnesium/silver, magnesium/indium and lithium/aluminum. The composition of the alloy is controlled by the temperature of the source of vaporization, the atmosphere and the degree of vacuum, and a suitable composition is selected. The anode and the cathode may be formed with a structure having two or more layers, where necessary.

In the organic EL device of the present invention, it is preferable that at least one face is sufficiently transparent in the region of the wavelength of the light emitted by the device so that the light emission is achieved efficiently. It is preferable that the substrate is also transparent. For the transparent electrode, the conditions in the vapor deposition or the sputtering are set so that the prescribed transparency is surely obtained using the above electrically conductive material. It is preferable that the electrode of the light emitting face has a transmittance of light of 10% or greater.

The substrate is not particularly limited as long as the substrate has the mechanical and thermal strength and is transparent. Examples of the substrate include glass substrates and transparent films of resins. Examples of the transparent film of a resin include films of polyethylene, ethylene-vinyl acetate copolymers, ethylene-vinyl alcohol copolymers, polypropylene, polystyrene, polymethyl methacrylate, polyvinyl chloride, polyvinyl alcohol, polyvinyl butyral, nylon, polyether ether ketones, polysulfones, polyether sulfones, tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoroethylene, polyvinylidene fluoride, polyesters, polycarbonates, polyurethanes, polyimides, polyether imides, polyimides and polypropylene.

For the formation of each layer of the organic EL device of the present invention, any of the dry processes of film formation such as the vacuum vapor deposition, the sputtering, the plasma plating and the ion plating and the wet processes of film formation such as the spin coating, the dipping and the flow coating, can be applied. The thickness of each film is not particularly limited. However, it is necessary that the thickness of the film be set at a suitable value. When the thickness is excessively great, application of a higher voltage is necessary to obtain the same output of the light, and the efficiency of light emission decreases. When the thickness is excessively small, pin holes are formed, and sufficient light emission cannot be obtained even when an electric field is applied. In general, a thickness in the range of 5 nm to 10 µm is suitable, and a thickness in the range of 10 nm to 0.2 µm is preferable.

When the wet process of film formation is used, the material forming each layer is dissolved or suspended in a suitable solvent such as ethanol, chloroform, tetrahydrofuran and dioxane, and a thin film is formed from the obtained solution or suspension. Any of the above solvents can be used. For any of the layers, suitable resins and additives may be used to improve the property for film formation and to prevent formation of pin holes in the film. Examples of the resin which can be used include insulating resins such as polystyrene, polycarbonates, polyarylates, polyesters, polyamides, polyurethanes, polysulfones, polymethyl methacrylate, polymethyl acrylate, cellulose and copolymers of these resins; photoconductive resins such as poly-N-vinylcarbazole and polysilanes; and electrically conductive resins such as polythiophene and polypyrrol. Examples of the additive include antioxidants, ultraviolet light absorbents and plasticizers.

In the organic EL device of the present invention, the property for sublimation of the aromatic compound is enhanced without adverse effects on the purity of color of the organic EL device by utilizing the aromatic compound of the present invention having the alkyl group exhibiting a great excluded volume effect. Therefore, the device can be prepared under a milder condition, and the prepared device exhibits excellent purity of color, provides great luminance of emitted light and efficiency of light emission, has a long lifetime and emits reddish light.

The organic EL device of the present invention exhibits more excellent purity of color and provides greater luminance of emitted light and efficiency of light emission even at a small driving voltage than those of conventional devices since the aromatic compound in which electron donating substituents are further introduced to diphenylamino group bonded to the mother skeleton structure is utilized. Moreover, the property for sublimation of the aromatic compound is enhanced without adverse effects on the purity of color since the bulky alkyl substituents are introduced into the aromatic compound described above, and the device can be prepared under a milder condition.

The organic EL device can be advantageously used for a planar light emitting member such as a flat panel display of wall televisions, a back light of copiers, printers and liquid crystal displays, a light source for instruments, a display panel, a marking light and an accessory.

The present invention will be described more specifically with reference to examples in the following.

PREPARATION EXAMPLE 1

Synthesis of Compounds (101) and (101')

The equation exhibiting the chemical reaction in the route of synthesis of Compounds (101) and (101') is shown in the following.

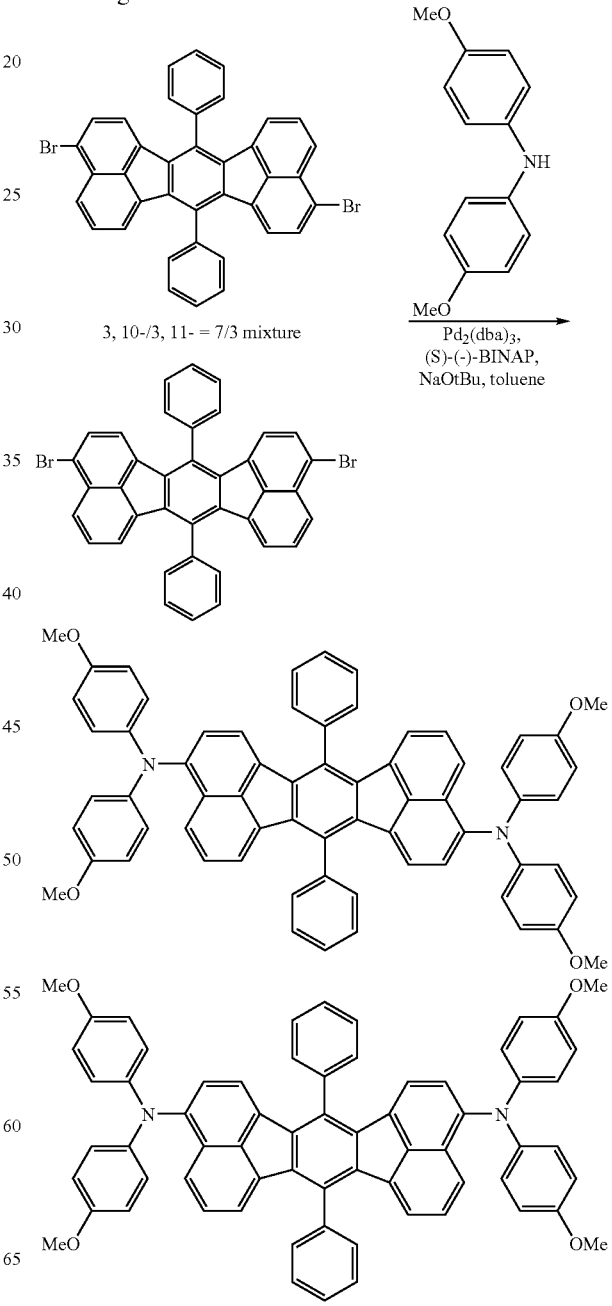

Into a 100 ml three-necked flask, 3.0 g (4.72 mmol) of a mixture of 3,10-dibromo-7,14-diphenylacenaphtho[1.2-k]fluoranthene and 3,11-dibromo-7,14-diphenylacenaphtho[1.2-k]fluoranthene (the ratio of the amounts: 7:3), 2.38 g (10.38 mmol) of 4,4'-dimethoxydiphenylamine, 64 mg (0.07 mmol) of tris(dibenzylideneacetone)dipalladium(0), 88 mg (0.14 mmol) of (S)-(−)-BINAP (2,2'-bis(diphenylphosphino)-1,1'-binaphthyl) and 1.1 g (11.4 mmol) of sodium t-butoxide were placed. After the flask was purged with argon, 50 ml of dehydrated toluene was added. The temperature of the resultant mixture was elevated to 110° C. under stirring, and the mixture was stirred further for 7 hours. After the reaction was completed, the reaction mixture was cooled to the room temperature, and 50 ml of dichloromethane was added. After being stirred at the room temperature for some time, the resultant mixture was filtered. The filtrate was concentrated, and the object compound was separated in accordance with the silica gel column chromatography using dichloromethane as the solvent. The solvent was removed, and the obtained residue was recrystallized from a mixed solvent containing toluene and ethanol. The formed crystals were separated by filtration and dried, and 3.6 g (3.86 mmol) of Compounds (101) and (101') were obtained (the yield: 82%). Compounds (101) and (101') obtained above were purified by degassing at 350° C. under $5.0 \times 10^{-6}$ Torr, and a purple powder was obtained.

The results of the field desorption (FD) mass analysis and the measurement of the purity in accordance with HPLC of Compounds (101) and (101') obtained above are shown in the following.

FD mass analysis: 932 ($M^+$, bp), 466 ($M^{2+}$) Purity in accordance with HPLC: 95%

PREPARATION EXAMPLE 2

Synthesis of Compounds (108) and (108')

The equation exhibiting the chemical reaction in the route of synthesis of Compounds (108) and (108') is shown in the following.

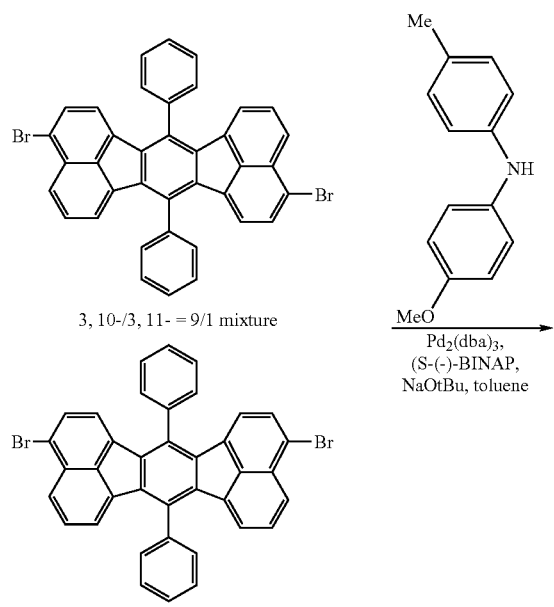

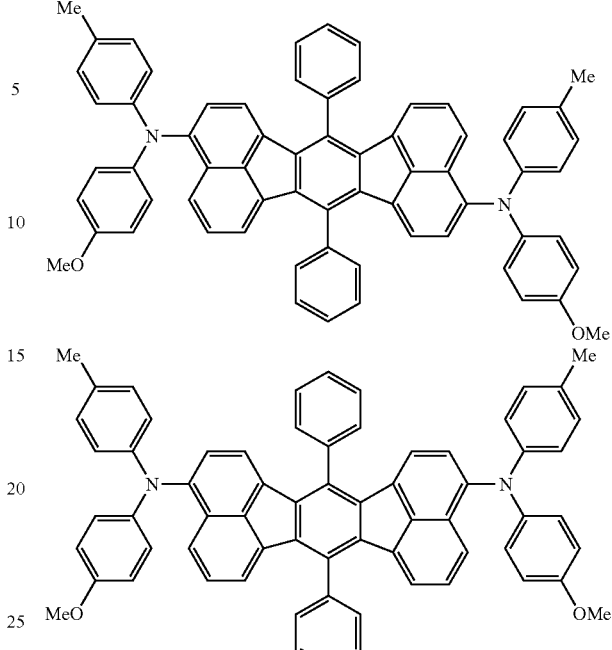

Into a 100 ml three-necked flask, 3.0 g (4.72 mmol) of a mixture of 3,10-dibromo-7,14-diphenylacenaphtho[1.2-k]fluoranthene and 3,11-dibromo-7,14-diphenylacenaphtho[1.2-k]fluoranthene (the ratio of the amounts: 9:1), 2.21 g (10.38 mmol) of (4-methoxyphenyl)-p-tolylamine, 64 mg (0.07 mmol) of tris(dibenzylideneacetone)dipalladium(0), 88 mg (0.14 mmol) of (S)-(−)-BINAP and 1.1 g (11.4 mmol) of sodium t-butoxide were placed. After the flask was purged with argon, 50 ml of toluene was added. The temperature of the resultant mixture was elevated to 110° C. under stirring, and the mixture was stirred further for 7 hours. After the reaction was completed, the reaction mixture was cooled to the room temperature, and 50 ml of dehydrated toluene was added. After being stirred at the room temperature for some time, the resultant mixture was filtered. The residue was washed with small amounts of water and dichloromethane, successively, and dried at 60° C. The filtrate was washed with water, and the organic layer was separated and dried with magnesium sulfate. The organic layer was filtered and concentrated. The obtained residue was combined with the residue separated and dried above. The combined residues were recrystallized from a mixed solvent containing toluene and ethanol. The formed crystals were separated by filtration and dried, and 3.2 g (3.56 mmol) of Compounds (108) and (108') were obtained (the yield: 75%). Compounds (108) and (108') obtained above were purified by degassing at 350° C. under $6.4 \times 10^{-6}$ Torr, and a dark red powder was obtained.

The results of the FD mass analysis and the measurement of the purity in accordance with HPLC of Compounds (108) and (108') obtained above are shown in the following.

FD mass analysis: 900 ($M^+$, bp), 450 ($M^{2+}$) Purity in accordance with HPLC: 98%

PREPARATION EXAMPLE 3

Synthesis of Compounds (504) and (504')

The equation exhibiting the chemical reaction in the route of synthesis of Compounds (504) and (504') is shown in the following.

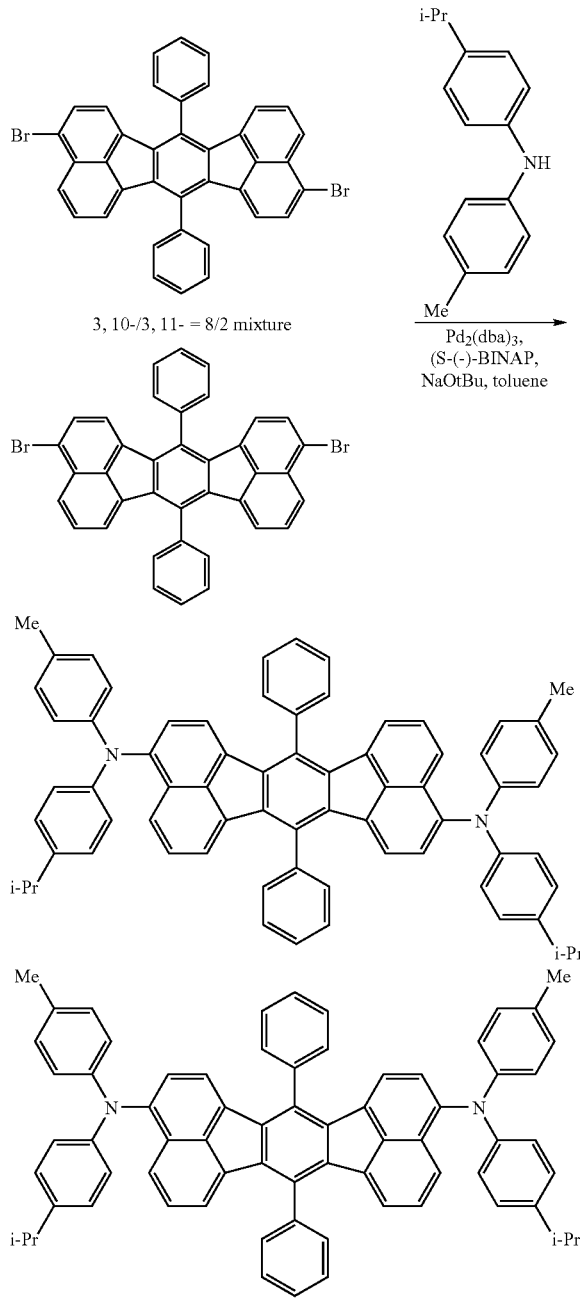

Into a 100 ml three-necked flask, 2.0 g (3.15 mmol) of a mixture of 3,10-dibromo-7,14-diphenylacenaphtho[1.2-k]fluoranthene and 3,11-dibromo-7,14-diphenylacenaphtho[1.2-k]fluoranthene (the ratio of the amounts: 8:2), 1.80 g (7.99 mmol) of (4-isopropylphenyl)-p-tolylamine, 44 mg (0.047 mmol) of tris(dibenzylideneacetone)dipalladium(0), 59 mg (0.095 mmol) of (S)-(−)-BINAP and 848 mg (8.82 mmol) of sodium t-butoxide were placed. After the flask was purged with argon, 50 ml of dehydrated toluene was added. The temperature of the resultant mixture was elevated to 115° C. under stirring, and the mixture was stirred further for 7.5 hours. After the reaction was completed, the reaction mixture was cooled to the room temperature, and 50 ml of dichloromethane was added. After being stirred at the room temperature for some time, the resultant mixture was filtered. The residue was washed with water and dichloromethane, successively. The filtrate was transferred to a separation funnel. The separated organic layer was dried with magnesium sulfate and filtered, and the solvent was removed by distillation. The obtained residue was separated and purified in accordance with the chromatography using 50 g of silica gel and a mixed solvent containing dichloromethane and toluene in relative amounts of 3:1. After being concentrated, the obtained fraction was recrystallized from a mixed solvent containing toluene and ethanol. The formed crystals were separated by filtration and dried, and 2.3 g (2.49 mmol) of Compounds (504) and (504') were obtained (the yield: 79%). Compounds (504) and (504') obtained above in an amount of 1.0 g were sublimed at 450° C. under $5.6 \times 10^{-6}$ Torr. The compounds were quickly sublimed in 1.5 hours, and a red product purified by sublimation was obtained.

The results of the FD mass analysis and the measurement of the purity in accordance with HPLC of Compounds (504) and (504') obtained above are shown in the following.

FD mass analysis: 940 ($M^+$, bp) Purity in accordance with HPLC: 98%

PREPARATION EXAMPLE 4

Synthesis of Compounds (501) and (501')

The equation exhibiting the chemical reaction in the route of synthesis of Compounds (501) and (501') is shown in the following.

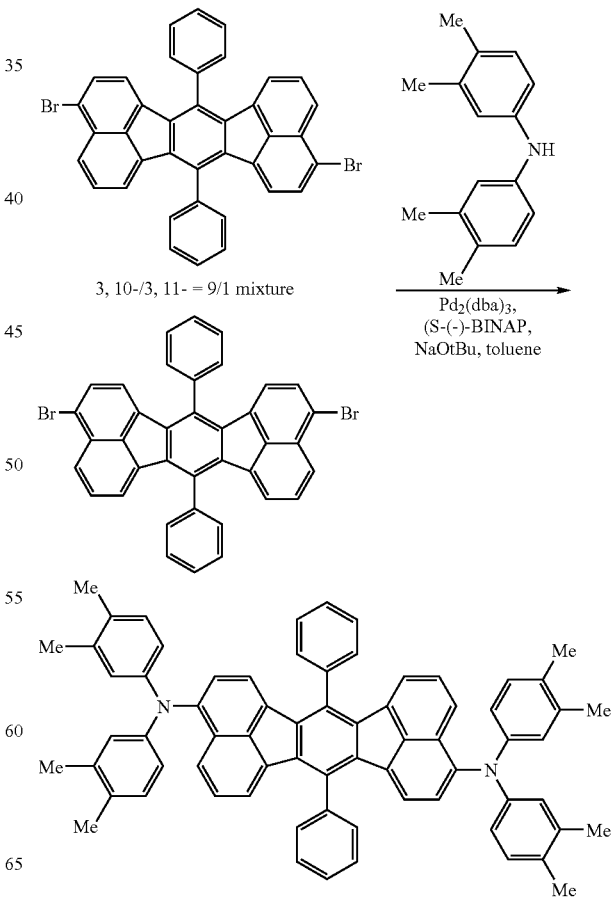

-continued

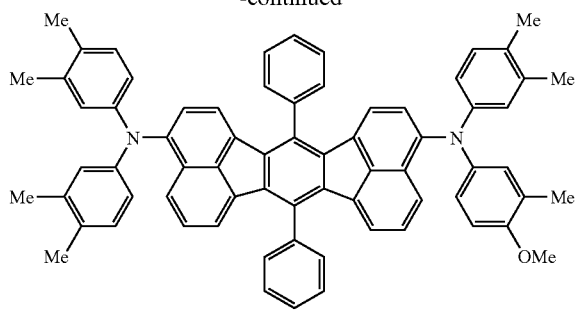

Into a 100 ml three-necked flask, 2.0 g (3.15 mmol) of a mixture of 3,10-dibromo-7,14-diphenylacenaphtho[1.2-k]fluoranthene and 3,11-dibromo-7,14-diphenylacenaphtho[1.2-k]fluoranthene (the ratio of the amounts: 8:2), 1.63 g (7.25 mmol) of bis(3,4-dimethyldiphenyl)amine, 44 mg (0.047 mmol) of tris(dibenzylideneacetone)dipalladium(0), 59 mg (0.095 mmol) of (S)-(−)-BINAP and 757 mg (7.88 mmol) of sodium t-butoxide were placed. After the flask was purged with argon, 50 ml of dehydrated toluene was added. The temperature of the resultant mixture was elevated to 120° C. under stirring, and the mixture was stirred further for 7 hours. After the reaction was completed, the reaction mixture was cooled to the room temperature, and 50 ml of dichloromethane was added. After being stirred at the room temperature for some time, the resultant mixture was filtered. The residue was washed with water and dichloromethane, successively. The filtrate was transferred to a separation funnel. The separated organic layer was dried with magnesium sulfate and filtered, and the solvent was removed by distillation. The obtained residue was recrystallized from a mixed solvent containing toluene and ethanol. The formed crystals were separated by filtration and dried, and 1.77 g (1.92 mmol) of Compounds (501) and (501') were obtained (the yield: 61%). Compounds (501) and (501') obtained above were sublimed at 420° C. under $4.6 \times 10^{-6}$ Torr. The compounds were quickly sublimed in 1.5 hours, and a red product purified by sublimation was obtained.

The results of the FD mass analysis and the measurement of the purity in accordance with HPLC of Compounds (501) and (501') obtained above are shown in the following.

FD mass analysis: 924 ($M^+$, bp) Purity in accordance with HPLC: 98%

COMPARATIVE EXAMPLE 1

A compound represented by general formula (I) in which four of $X_1$ to $X_{20}$ represent methyl group and the others represent hydrogen atom was prepared. The purification by sublimation of the prepared compound was attempted at 460° C. under $4.2 \times 10^{-6}$ Torr. The rate of the sublimation was small, and the sublimation of the entire amount was difficult after 3 hours. Thus, the above compound had the property of sublimation inferior to that of Compounds (504), (504'), (501) and (501') of the compounds of the present invention.

EXAMPLE 1

Preparation of an Organic EL Device (Compounds (101) and (101'))

A transparent electrode composed of indium tin oxide was formed on a glass substrate of a size of 25 mm×75 mm×1.1 mm thickness. The glass substrate was cleaned by application of ultrasonic wave and exposure to ozone, and the cleaned glass substrate was attached to a vacuum vapor deposition apparatus.

After the compound TPD 74 shown in the following was vapor deposited on the surface of the cleaned substrate in a manner such that the formed film had a thickness of 60 nm, the compound NPD shown in the following was vapor deposited on the formed film in a manner such that the formed film had a thickness of 20 nm. Then, Compounds (101) and (101') obtained in Preparation Example 1 and Alq (an aluminum complex of 8-hydroxyquinoline) as the light emitting materials in amounts such that the ratio of the amounts by weight was 3:10, i.e., the content of Compounds (101) and (101') was 12.9% by weight, were simultaneously vapor deposited in a manner such that the formed film had a thickness of 50 nm. On the formed film, Alq was vapor deposited in a manner such that the formed film had a thickness of 10 nm. The films of TPD 74, NPD, Compounds (101) and (101'):Alq and Alq worked as the hole injection layer, the hole transport layer, the light emitting medium layer and the electron injection layer, respectively.

On the films formed above, LiF as an alkali metal halide was vapor deposited in a manner such that the formed film had a thickness of 0.2 nm, and then aluminum was vapor deposited in a manner such that the formed film had a thickness of 150 nm. The films of Al/LiF worked as the cathode. Thus, an organic EL device was prepared.

The obtained device was tested by passing an electric current. Red light was emitted at a luminance of 104 cd/m² under a voltage of 6.7 V and a current density of 8.6 mA/cm². The chromaticity coordinates were (0.67, 0.33), and the current efficiency of light emission was 1.20 cd/A.

TPD-74

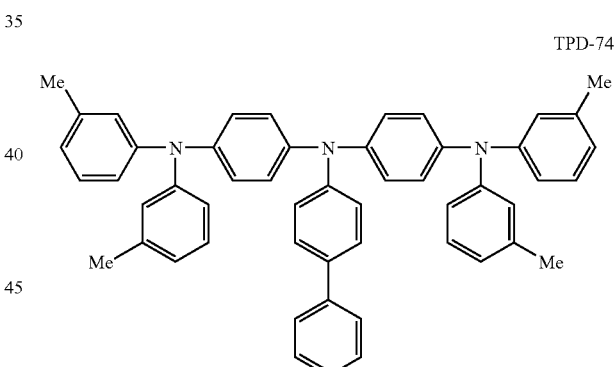

NPD

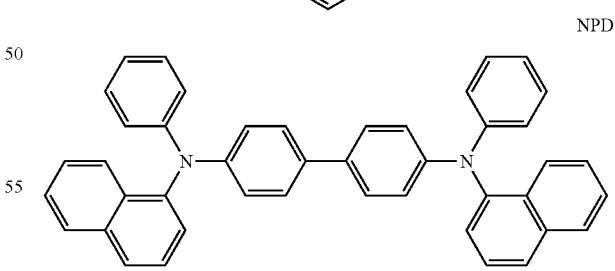

EXAMPLE 2

Preparation of an Organic EL Device (Compounds (108) and (108'))

An organic EL device was prepared in accordance with the same procedures as those conducted in Example 1 except that, in place of Compounds (101) and (101'), Compounds (108) and (108') obtained in Preparation Example 2 were used in amounts such that the content of Compounds (108) and (108') was 13.3% by weight.

The obtained device was tested by passing an electric current. Red light was emitted at a luminance of 96.6 cd/m$^2$ under a voltage of 5.2 V and a current density of 4.80 mA/cm$^2$. The chromaticity coordinates were (0.66, 0.34), and the current efficiency of light emission was 2.01 cd/A.

EXAMPLE 3

Preparation of an Organic EL Device (Compounds (504) and (504'))

An organic EL device was prepared in accordance with the same procedures as those conducted in Example 1 except that, in place of Compounds (101) (101'), Compounds (504) and (504') obtained in Preparation Example 3 were used in amounts such that the content of Compounds (504) and (504') was 13.0% by weight.

The obtained device was tested by passing an electric current. Red light was emitted at a luminance of 117 cd/m$^2$ under a voltage of 5.5 V and a current density of 4.08 mA/cm$^2$. The chromaticity coordinates were (0.64, 0.36), and the current efficiency of light emission was 2.87 cd/A.

EXAMPLE 4

Preparation of an Organic EL Device (Compounds (501) and (501'))

An organic EL device was prepared in accordance with the same procedures as those conducted in Example 1 except that, in place of Compounds (101) and (101'), Compounds (501) and (501') obtained in Preparation Example 4 were used in amounts such that the content of Compounds (501) and (501') was 13.0% by weight.

The obtained device was tested by passing an electric current. Red light was emitted at a luminance of 127 cd/m$^2$ under a voltage of 5.8 V and a current density of 5.74 mA/cm$^2$. The chromaticity coordinates were (0.65, 0.35), and the current efficiency of light emission was 2.21 cd/A.

COMPARATIVE EXAMPLE 2

Preparation of an Organic EL Device (Compound Ru2)

An organic EL device was prepared in accordance with the same procedures as those conducted in Example 1 except that Compound Ru2 shown in the following and Alq were used as the light emitting materials and simultaneously vapor deposited in amounts such that the ratio of the amounts by weight was 1:40, i.e., the content of Compound Ru2 was 2.0% by weight.

The obtained device was tested by passing an electric current. A current of 28.0 mA/cm$^2$ flowed under a voltage of 10 V This shows that the above device required a greater applied voltage than that of the devices in Examples 1 to 4.

The luminance was 116 cd/m$^2$, the current efficiency of light emission was 0.41 cd/A and the chromaticity coordinates were (0.67, 0.32). The efficiency of light emission was markedly smaller than those of the devices in Examples 1 to 4.

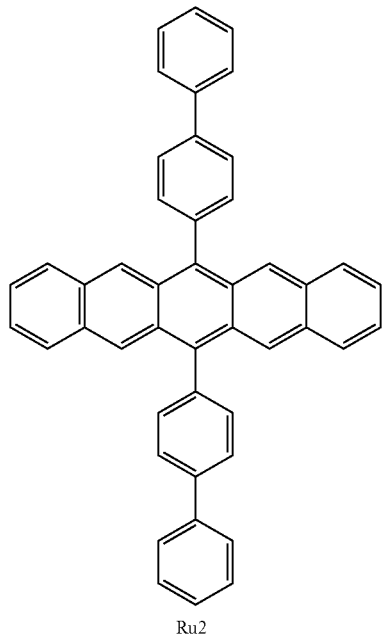

Ru2

COMPARATIVE EXAMPLE 3

Preparation of an Organic EL Device (the Compound of Comparative Example 1)

An organic EL device was prepared in accordance with the same procedures as those conducted in Example 1 except that the compound represented by general formula (I) in which four of $X_1$ to $X_{20}$ represent methyl group and the others represent hydrogen atom and Alq as the light emitting materials were simultaneously vapor deposited in amounts such that the ratio of the amounts by weight was 10:1, i.e., the content of the compound of Comparative Example 1 was 5.29% by weight.

The obtained device was tested by passing an electric current. Reddish orange light was emitted at a luminance of 106 cd/m$^2$ under a voltage of 6.5 V and a current density of 3.78 mA/cm$^2$. The chromaticity coordinates were (0.62, 0.38), and the current efficiency of light emission was 2.8 cd/A. The color was reddish orange and the purity of color was inferior to those in Examples 1 to 4 although the applied voltage and the efficiency of light emission were about the same.

INDUSTRIAL APPLICABILITY

As described in detail in the above, the organic EL device of the present invention can be prepared under mild conditions since the novel aromatic compound in which the electron donating substituent is introduced to diphenylamino group bonded to the mother skeleton structure and the bulky alkyl substituents is introduced is utilized, and the prepared device exhibits excellent purity of color, provides great luminance of emitted light and efficiency of light emission, has a long lifetime and emits reddish color.

The invention claimed is:

1. An organic electroluminescence device which emits reddish light and comprises a pair of electrodes and an organic compound layer which comprises a light emitting layer or a plurality of layers comprising a light emitting layer and is disposed between the pair of electrodes, wherein at least one layer in the organic compound layer comprises an aromatic compound represented by general formula (I):

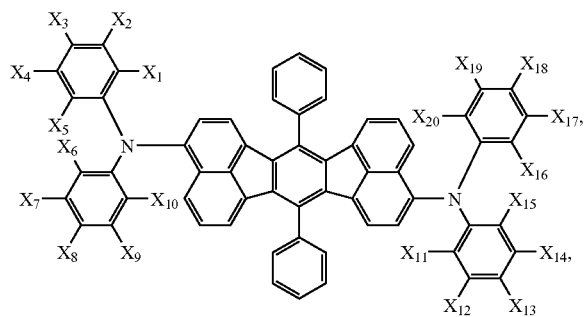

or formula (I'):

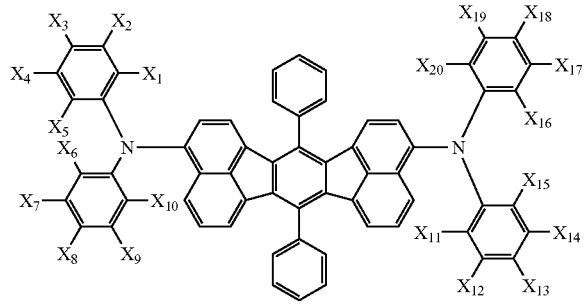

wherein general formulae (I) and (I') satisfy any one of following conditions (1) to (4):

(1) Among $X_1$ to $X_{20}$, at least four each independently represent a linear or branched alkoxyl group having 1 to 6 carbon atoms, and others each represent hydrogen atom;

(2) Among $X_1$ to $X_{20}$, at least one represents a linear or branched alkyl group having 1 to 6 carbon atoms, at least one represents a linear or branched alkoxyl group having 1 to 6 carbon atoms, a total of a number of the alkyl group and a number of the alkoxyl group being 4 or greater, and others each represent hydrogen atom;

(3) Among $X_1$ to $X_{20}$, at least six each independently represent a linear or branched alkyl group having 1 to 6 carbon atoms, and others each represent hydrogen atom; and (4) Among $X_1$ to $X_{20}$, at least four each independently represent a linear or branched alkyl group having 1 to 6 carbon atoms, two alkyl groups among said alkyl groups having 3 to 6 carbon atoms, and others each represent hydrogen atom.

2. An organic electroluminescence device according to claim 1, wherein the organic compound layer is at least one of a hole transport layer and a light emitting layer.

3. An organic electroluminescence device according to claim 1, wherein the organic compound layer comprises 1 to 70% by weight of the aromatic compound represented by general formula (I) or (I').

4. An organic electroluminescence device according to claim 2, which comprises an inorganic compound layer disposed between the organic compound layer and the electrode.

* * * * *